United States Patent
Wu et al.

(10) Patent No.: US 12,245,845 B2
(45) Date of Patent: Mar. 11, 2025

(54) SYSTEM AND METHOD FOR HEART RATE MEASUREMENT USING FACIAL VIDEO

(71) Applicants: UNIVERSITY OF MARYLAND, COLLEGE PARK, College Park, MD (US); NORTH CAROLINA STATE UNIVERSITY, Raleigh, NC (US)

(72) Inventors: Min Wu, Clarksville, MD (US); Chau-Wai Wong, Apex, NC (US); Mingliang Chen, College Park, MD (US); Qiang Zhu, College Park, MD (US); Zachary Lazri, Gaithersburg, MD (US)

(73) Assignees: UNIVERSITY OF MARYLAND, COLLEGE PARK, College Park, MD (US); NORTH CAROLINA STATE UNIVERSITY, Raleigh, NC (US)

( * ) Notice: Subject to any disclaimer, the term of this patent is extended or adjusted under 35 U.S.C. 154(b) by 730 days.

(21) Appl. No.: 17/458,170

(22) Filed: Aug. 26, 2021

(65) Prior Publication Data
US 2021/0386307 A1 Dec. 16, 2021

Related U.S. Application Data

(63) Continuation-in-part of application No. 16/647,233, filed as application No. PCT/US2018/051342 on Sep. 17, 2018, now Pat. No. 11,501,430.
(Continued)

(51) Int. Cl.
G06K 9/00 (2022.01)
A61B 5/00 (2006.01)
(Continued)

(52) U.S. Cl.
CPC ........ *A61B 5/02416* (2013.01); *A61B 5/7207* (2013.01); *A61B 5/725* (2013.01);
(Continued)

(58) Field of Classification Search
CPC ......... G06K 9/00; A61B 5/7253; A61K 35/12
(Continued)

(56) References Cited

U.S. PATENT DOCUMENTS

2013/0245462 A1 9/2013 Capdevila et al.
2016/0106329 A1 4/2016 Hoof et al.
(Continued)

OTHER PUBLICATIONS

International Search Report and Written Opinion dated Jan. 16, 2019 corresponding to International Patent Application No. PCT/US2018/051342. No copy provided, per MPEP 609. Copy submitted in parent U.S. Appl. No. 16/647,233.

*Primary Examiner* — Seyed H Azarian
(74) *Attorney, Agent, or Firm* — SQUIRE PATTON BOGGS (US) LLP

(57) ABSTRACT

Systems, methods, apparatuses, and computer program products for contact-free heart rate monitoring and/or measurement are provided. One method may include receiving video(s) that include visual frame(s) of individual(s) performing exercises, detecting some exposed skin from the video(s), and performing motion compensation to generate color signals for the exposed skin to precisely align frames of the exposed skin. The method may also include generating the color signals by estimating a skin color for each frame by taking a spatial average over pixels of a cheek of the face(s) for R, G, and B channels, respectively, applying an operation to remove remaining motion traces from the frames such that the heart rate traces dominate, and extracting and/or outputting the heart rate of the individuals using a frequency estimator of the skin color signals.

18 Claims, 10 Drawing Sheets

Related U.S. Application Data

(60) Provisional application No. 62/559,182, filed on Sep. 15, 2017, provisional application No. 63/070,771, filed on Aug. 26, 2020.

(51) Int. Cl.
| | |
|---|---|
| *A61B 5/024* | (2006.01) |
| *A61K 35/12* | (2015.01) |
| *G06N 3/02* | (2006.01) |
| *G06T 3/00* | (2006.01) |
| *G06T 7/20* | (2017.01) |
| *G06T 7/90* | (2017.01) |
| *G16H 30/40* | (2018.01) |

(52) U.S. Cl.
CPC ............. *A61B 5/7264* (2013.01); *G06N 3/02* (2013.01); *G06T 3/00* (2013.01); *G06T 7/20* (2013.01); *G06T 7/90* (2017.01); *G16H 30/40* (2018.01); *A61B 2576/02* (2013.01); *G06T 2207/10016* (2013.01); *G06T 2207/10024* (2013.01); *G06T 2207/20076* (2013.01); *G06T 2207/20084* (2013.01); *G06T 2207/30088* (2013.01); *G06T 2207/30201* (2013.01)

(58) Field of Classification Search
USPC ........ 382/100, 103, 106–107, 108, 115, 118, 382/128, 156, 165, 168, 173, 181, 199, 382/224, 254, 260–261, 274–276, 382/286–291, 312, 321; 600/323, 317, 600/322
See application file for complete search history.

(56) References Cited

U.S. PATENT DOCUMENTS

| | | | |
|---|---|---|---|
| 2016/0113531 A1* | 4/2016 | Visvanathan | A61B 5/02438 600/323 |
| 2016/0278644 A1 | 9/2016 | He | |
| 2016/0317041 A1 | 11/2016 | Porges et al. | |
| 2017/0238805 A1* | 8/2017 | Addison | A61B 5/7221 |
| 2018/0070887 A1* | 3/2018 | Lee | A61B 5/0004 |
| 2020/0085312 A1* | 3/2020 | Tzvieli | A61B 5/02055 |
| 2020/0337623 A1* | 10/2020 | Bulut | A61B 5/7275 |
| 2023/0033353 A1* | 2/2023 | Cendrillon | A61B 5/02416 |

* cited by examiner (a)

(b)

SYSTEM AND METHOD FOR HEART RATE MEASUREMENT USING FACIAL VIDEO

CROSS-REFERENCE TO RELATED APPLICATIONS

This application claims priority from U.S. provisional patent application No. 63/070,771 filed on Aug. 26, 2020, and this application is a continuation-in-part of U.S. application Ser. No. 16/647,233 filed on Mar. 13, 2020, which is a 371 of PCT/US2018/051342 filed on Sep. 17, 2018, which claims priority from U.S. provisional patent application No. 62/559,182 filed on Sep. 15, 2017. The contents of these earlier filed applications are hereby incorporated by reference in their entirety.

GOVERNMENT SUPPORT

This invention was made with government support under ECCS1309623, CCF1320803, and CNS1848835 awarded by the National Science Foundation. The government has certain rights in the invention.

FIELD

Some example embodiments may relate to methods, apparatuses, and/or systems for contact-free monitoring of heart rate(s) using videos of people.

BACKGROUND

Heart monitoring or cardiac monitoring generally includes intermittent or continuous monitoring of heart activity or rhythm. In most instances, cardiac monitoring is performed by electrocardiography that includes recording the electrical activity of the heart over a period of time using electrodes placed over the skin. The electrodes are able to detect the electrical changes on the skin that arise from the heart's electrophysiologic pattern during each heartbeat. Other heart rate monitors, such as chest belts, finger clips, or smartwatches, can monitor heart rate by contacting different parts of an individual's body.

More recently, contact-free methods for monitoring heart rate have been developed. These methods can be a more user-friendly approach than conventional contact-based methods, such as electrodes, chest belts, or finger clips. However, thus far, contact-free heart rate monitoring has not been sufficiently accurate for capturing heart rates using videos of human faces.

SUMMARY

One embodiment is directed to a method for contactless measurement of heart rate. The method may include receiving one or more video(s) that may include visual frames of one or more individual(s) performing exercises, detecting at least some exposed skin from the individual(s) in the video(s), and performing motion compensation to generate skin color signals for the detected exposed skin. In an embodiment, the performing of the motion compensation comprises performing motion compensation for precisely aligning frames of the detected exposed skin. The method may also include generating the skin color signals using the precisely aligned frames of the detected exposed skin, where the generating comprises estimating a skin color for each frame by taking a spatial average over pixels of at least a portion of the exposed skin for R, G, and B channels, respectively. The method may then include applying an operation to remove remaining motion traces from the frames such that the heart rate traces dominate, and extracting and/or outputting the heart rate of the individuals using a frequency estimator of the skin color signals.

Another embodiment is directed to an apparatus for contactless measurement of heart rate. The apparatus may include at least one processor and at least one memory comprising computer program code. The at least one memory and computer program code may be configured, with the at least one processor, to cause the apparatus at least to receive one or more video(s) that may include visual frames of one or more individual(s) performing exercises, detect at least some exposed skin from the individual(s) in the video(s), and perform motion compensation to generate skin color signals for the detected exposed skin. In an embodiment, the performing of the motion compensation comprises performing motion compensation for precisely aligning frames of the detected exposed skin. The at least one memory and computer program code may be configured, with the at least one processor, to cause the apparatus at least to generate the skin color signals using the precisely aligned frames of the detected exposed skin, where the generating comprises estimating a skin color for each frame by taking a spatial average over pixels of at least a portion of the exposed skin for R, G, and B channels, respectively. The at least one memory and computer program code may be configured, with the at least one processor, to cause the apparatus at least to apply an operation to remove remaining motion traces from the frames such that the heart rate traces dominate, and extract and/or output the heart rate of the individuals using a frequency estimator of the skin color signals.

Another embodiment is directed to an apparatus for contactless measurement of heart rate. The apparatus may include receiving means for receiving one or more video(s) that may include visual frames of one or more individual(s) performing exercises, detecting means for detecting at least some exposed skin from the individual(s) in the video(s), and performing means for performing motion compensation to generate skin color signals for the detected exposed skin. In an embodiment, the performing means comprises means for performing motion compensation for precisely aligning frames of the detected exposed skin. The apparatus may also include generating means for generating the skin color signals using the precisely aligned frames of the detected exposed skin, where the generating means comprises means for estimating a skin color for each frame by taking a spatial average over pixels of at least a portion of the exposed skin for R, G, and B channels, respectively. The apparatus may also include applying means for applying an operation to remove remaining motion traces from the frames such that the heart rate traces dominate, and extracting means for extracting and/or outputting the heart rate of the individuals using a frequency estimator of the skin color signals.

Another embodiment is directed to computer readable medium comprising program instructions stored thereon for performing a method. The method may include receiving one or more video(s) that may include visual frames of one or more individual(s) performing exercises, detecting at least some exposed skin from the individual(s) in the video(s), and performing motion compensation to generate skin color signals for the detected exposed skin. In an embodiment, the performing of the motion compensation comprises performing motion compensation for precisely aligning frames of the detected exposed skin. The method may also include generating the skin color signals using the precisely aligned frames of the detected exposed skin, where the generating comprises estimating a skin color for each frame by taking a spatial average over pixels of at least a portion of the exposed skin for R, G, and B channels, respectively. The method may then include applying an operation to remove remaining motion traces from the frames such that the heart rate traces dominate, and extracting and/or outputting the heart rate of the individuals using a frequency estimator of the skin color signals.

Certain embodiments are directed to a method of remote photoplethysmography (rPPG) and/or a rPPG system. The method may include or the system may be caused to perform: receiving one or more videos that include visual frames of at least one subject performing physical activity, detecting at least one skin pixel from one or more of the visual frames of the at least one subject, processing three color channels in red, green and blue inside the detected at least one skin pixel to produce a pulse signal with a highest pulse signal-to-noise ratio (SNR), filtering, by a normalized least mean square filter, the pulse signal to produce a first level filtered pulse signal that is free of motion artifacts, using a frequency trace tracking method to track a pulse rate of the at least one subject based on the first level filtered pulse signal, reconstructing the pulse signal in a time domain to produce a second level filtered pulse signal, and estimating at least one of pulse rate or pulse rate variability of the at least one subject based at least on the second level filtered pulse signal.

BRIEF DESCRIPTION OF THE DRAWINGS

For proper understanding of example embodiments, reference should be made to the accompanying drawings, wherein.

DETAILED DESCRIPTION

Figure 1:
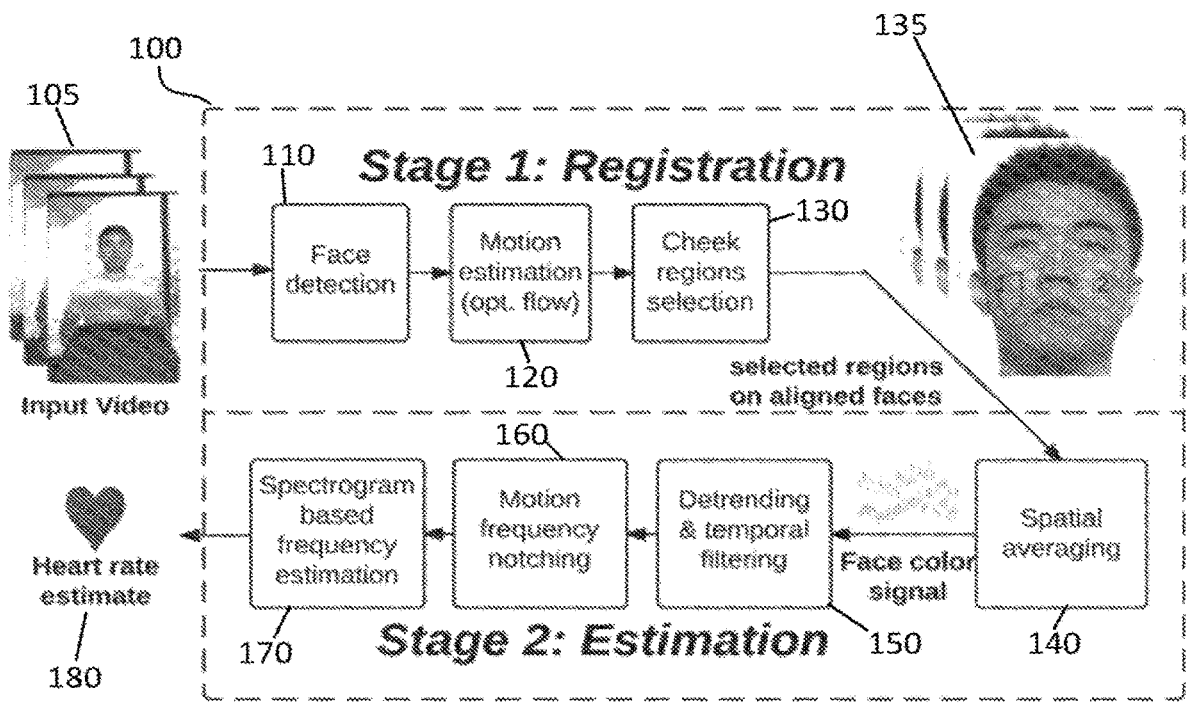
FIG. 1 illustrates an example block diagram of a heart rate monitoring system 100, according to an example embodiment.

It will be readily understood that the components of certain example embodiments, as generally described and illustrated in the figures herein, may be arranged and designed in a wide variety of different configurations. Thus, the following detailed description of some example embodiments of systems, methods, apparatuses, and computer program products for contact-free heart rate monitoring, is not intended to limit the scope of certain embodiments but is representative of selected example embodiments.

The features, structures, or characteristics of example embodiments described throughout this specification may be combined in any suitable manner in one or more example embodiments. For example, the usage of the phrases "certain embodiments," "some embodiments," or other similar language, throughout this specification refers to the fact that a particular feature, structure, or characteristic described in connection with an embodiment may be included in at least one embodiment. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain example embodiments, and not in limitation thereof.

Contact-free monitoring of the heart rate using videos of human faces or other exposed skin is a user-friendly approach compared to conventional contact based ones, such as the use of electrodes, chest belts, and/or finger clips. Such contact-free monitoring systems can extract, from a video of an individual's face, a 1-D sinusoid-like face color signal that has the same frequency as the individual's heartbeat. Thus, the ability to measure heart rate without touch-based sensors is an attractive approach and has the potential for beneficial applications in areas such as smart health and sports medicine.

To this point, measuring heart rate from videos has mostly focused on still or rest cases, or situations with relatively small body motions. In contrast, there has been little focus on measuring heart rate in large motion scenarios, such as during fitness exercises. Although it has been shown that, after using block-based motion estimation for an exercise video, a periodic signal can be extracted from the color in the face area. However, this was not verified against a reference signal and the accuracy of the estimated heart rate was not quantitatively determined.

Optimizing the adaptation and preparedness for enhanced performance is a goal of athletic training and recovery. The use of heart rate (HR) and heart rate variability (HRV) measures in sports represents a non-invasive, time-efficient method to monitor the training dose and quantify an athletes' response. With the context information of the training and proper interpretations of the HR measures, such practice has direct implications for adjusting the training load in order to harness individual or team training objectives in a safe and effective manner. As discussed below, certain embodiments provide a remote photoplethysmography (rPPG) system that is robust for purposes of pulse rate and/or pulse rate variability extraction from fitness face video, such as where the subject is exercising and/or the video contains large subject motions. Some embodiments provide an online learning scheme for precise subject- and scene-specific skin detection, and can use motion information as a cue to adaptively remove the motion-induced artifacts in the corrupt rPPG signal. In an embodiment, for pulse rate variability extraction, the accurate heart rate estimation is provided as feedback for a second-level pulse signal filtering. In certain embodiments, after the pulse filtering processing, the inter-beat intervals and/or pulse rate variability can be precisely estimated.

According to certain example embodiments, a contactless heart rate measurement system, apparatus and/or method are provided. Some embodiments may be used, for example, to extrapolate or determine a person's heart rate from videos of fitness exercises. An embodiment may be configured to capture possibly wildly varying heart rate through different stages of fitness exercises.

Some embodiments may relate generally to systems and methods for physiological measurements from video data. In certain embodiments, the system may be a remote photoplethysmography (rPPG) system. In certain embodiments, the system and method may be used to measure pulse rate and/or pulse rate variability. In certain embodiments, the system may include a camera. In certain embodiments, videos of a subject's face may be analyzed to measure variations in skin color. In certain embodiments, heart rate and/or heart rate variation data may be estimated using the variation measurements. In certain embodiments, the system and method may include correction mechanisms to account for a variety of noise sources, including subject movement or facial motion, changes in ambient environment, or natural variations in the subject's complexion. In certain embodiments, the system and method may further include features to protect the privacy and personal data of the subjects.

FIG. 1 illustrates an example block diagram of a heart rate monitoring system 100, according to an example embodiment. In an embodiment, the system 100 may take one or more videos 105 as an input. The video(s) 105 may include fitness or exercise videos, one or more facial images, or images of other exposed skin of a person. Fitness exercise videos may contain large and periodic motions. An embodiment provides a highly precise motion compensation scheme to allow generating a clean skin color signal or face color signal to facilitate latter analysis steps, and may use the resulting motion cue as a guide to adaptively remove ambiguous frequency components that can be substantially close to the heart rate. It is noted that certain embodiments discussed in the following utilize an individual's face as an example of exposed skin that can be utilized in the steps for measuring a person's heart rate. However, it should be understood that other embodiments are equally applicable to any exposed skin of a person's body part (not just the face). As such, example embodiments are not merely limited to detection and processing of the individual's face, but are similarly applicable to other body parts.

As illustrated in the example of FIG. 1, system 100 may include a face detection block 110 configured to detect face(s) (or other exposed skin) from the input video(s) 105. In an embodiment, system 100 may also include a motion estimation block 120 configured to perform highly precise pixel-level motion compensation. This precise pixel-level motion compensation is one important step toward generating a clean face color signal. In one embodiment, motion estimation block 120 may use an optical flow algorithm to find correspondences of all points on the faces between two frames. Optical flow uses gradient information to iteratively refine the estimated motion vector field.

In order to avoid being trapped in local optima, an embodiment may introduce a pre-alignment stage to bring the face images roughly aligned before conducting a fine-grain alignment using optical flow. Certain example embodiments may utilize the Viola--Jones face detector to obtain rough estimates of the location and size of the face. An example embodiment may clip and resize the face region of each frame, for example to 180 pixels in height, effectively generating a pre-aligned video for the face region. The pre-alignment may significantly reduce the lengths of motion vectors, which in turn makes results of optical flow more reliable. In one example, two face images may be likely to have a global color difference due to the heartbeat. In order to conduct a precise face alignment, instead of using the illumination consistency assumption that is widely used, an embodiment assumes more generally that the intensity I of a point in two frames are related by an affine model, namely:

$$I(x+\Delta x, y+\Delta y, t+1) = (1-\epsilon)I(x, y, t) + b \qquad (1)$$

where $\epsilon$ and b control the scaling and bias of the intensities between two frames. Both of them are usually small. Traditional techniques tackling the illumination consistency cases such as Taylor expansion and regularization can be similarly applied, according to certain embodiments. Mathematical analysis has shown that omitting the illumination change due to the heartbeat, and applying a standard optical flow method leads to a bias term that is at the same (or similar) order magnitude compared to the intrinsic error (in terms of standard deviation) of the optical flow system.

Figure 2:
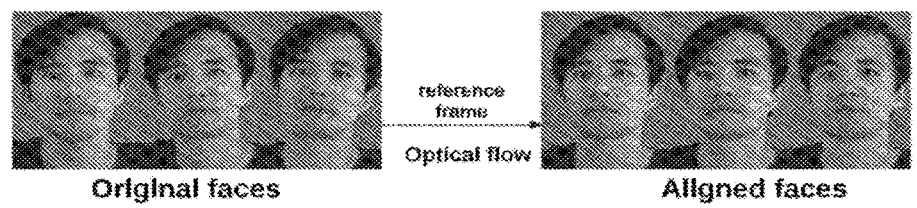
FIG. 2 illustrates an example of face images from a same segment before and after optical flow based motion compensation using the same reference, according to an example embodiment.

According to certain embodiments, each video may be divided into small temporal segments with one frame overlapping for successive segments. In an embodiment, the frame in the middle of the segment may be used as the reference for optical flow based motion compensation. This would ensure that two frames being aligned do not have significant occlusion due to long separation in time. FIG. 2 illustrates an example of face images from a same segment before and after optical flow based motion compensation using the same reference, according to an example embodiment.

As illustrated in the example of FIG. 1, system 100 may also include a segment continuity and cheek regions selection block 130 configured to select cheek regions and/or corresponding face landmarks. With precisely aligned face videos in short segments, an embodiment can estimate the face color for each frame by taking a spatial average over pixels of the cheek for R, G, and B channels, respectively. The three resulting 1-D time signals may be referred to as the face color signals.

When concatenating segments into color signals, the last point of the current segment and the first point of the next segment may have different intensities because they correspond to the same frame whose motion compensation were conducted with respect to two different references. To address this problem, according to an embodiment, the difference of the intensity between the two points may be calculated and the resulting value is used to bias the signal of the next segment in order to maintain the continuity. The face color signals may contain color change due to the heartbeat, and illumination change due to face motions such as tilting. In an embodiment, the green channel may be used because it corresponds to the absorption peak of (oxy-) hemoglobin that changes periodically as the heartbeat, and source separation methods such as the independent component analysis (ICA) may also be used to separate the heartbeat component. According to an embodiment, the fixed linear weights (−1,2,−1) may be used for R, G, B channels to best retain the heartbeat component while compensating the motion induced illumination change.

To determine the cheek regions for conducting spatial averaging 140, an example embodiment may construct two conservative regions that do not contain facial structures and are most upfront in order to avoid strong motion-induced specular illumination changes. Certain embodiments may then use identified facial landmarks to facilitate the construction of the cheek regions. In one embodiment, each cheek region may be constructed to be a polygon that has a safe margin to the facial structures protected by the landmarks. One example for such selected cheek regions and corresponding face landmarks is depicted on the face 135 illustrated in FIG. 1.

As further illustrated in the example of FIG. 1, system 100 may also include a de-trending and temporal filtering block 150 that may be configured to take the face color signal as input and remove illumination variation. It is noted that illumination variation can be caused by passersby and/or the gradual change of sunlight, for example, which can result in the face color signal to drift. This can be problematic for Fourier-based analysis. Such a slowly-varying trend can be estimated and then subtracted from a raw face color signal, $x_{raw} \in R^L$, where L is the length of the signal. The trend may be assumed to be a clean, unknown version of $x_{raw}$ with a property that its accumulated convexity measured for every point on the signal is as small as possible, namely:

$$\hat{x}_{trend} = \underset{x}{\operatorname{argmax}} \|x_{raw} - x\|^2 + \lambda \|D_2 x\|^2 \qquad (2)$$

where $\lambda$ is a regularization parameter controlling the smoothness of the estimated trend, and $D_2 \in R^{L \times L}$ is a spare toeplitz second-order difference matrix. The closed-form solution is $\hat{x}_{trend} = (I + \lambda D_2^T D_2)^{-1} x_{raw}$. Hence, the detrended signal is $x_{raw} - \hat{x}_{trend}$. After detrending, an embodiment may use a bandpass filter to reject the frequency components that are outside a normal range of human heart rate. In one example, the bandpass filter may be an IIR Butterworth with a passband from 40 to 240 bpm. In an embodiment, adaptive filtering may be applied using the analyzed motion information to mitigate the motion effect and output a signal containing the human heart rate trace with an improved signal-to-noise ratio.

In the above-described stages of the system 100 of FIG. 1, the impact of face motions is removed. For example, optical flow can be used to precisely align the faces, and a color weight vector that is least susceptible to motion may be used to reduce impact of the periodic illumination change, for example, due to the face tilting. As also illustrated in the example of FIG. 1, system 100 further includes a motion frequency notching block 160 that may be configured to apply a notching operation to remove any remaining trace due to motion. In an embodiment, motion information from the face tracker and the optical flow may be combined to generate two time signals, one for the x-direction and the other for the y-direction. For each time bin on the spectrogram, one embodiment may conduct two notch operations based on the dominating frequency estimated from the x- and y-motion components.

Figure 3:
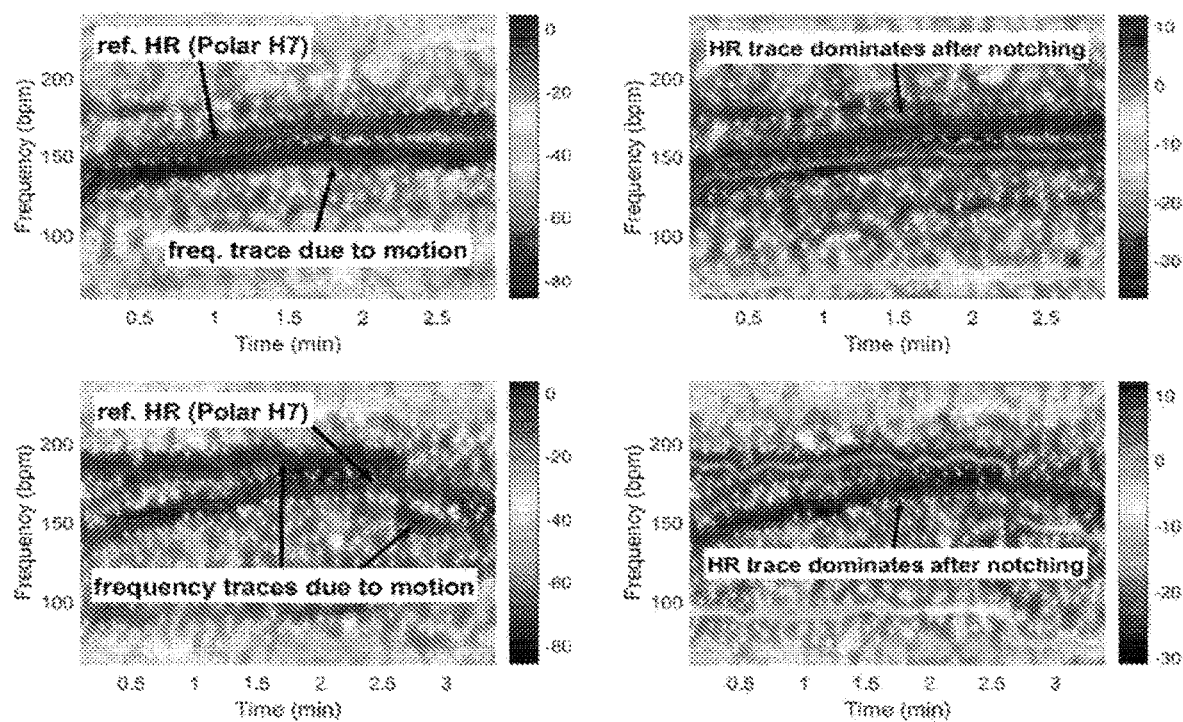
FIG. 3 illustrates an example of the contrast of spectrograms before and after notching the frequencies of fitness motions, according to certain embodiments.

FIG. 3 illustrates an example of the contrast of spectrograms before and after notching the frequencies of fitness motions, according to certain embodiments. Spectrograms in the left column of FIG. 3 show that motion traces exist before notching, as highlighted by the arrows. Motion artifacts can be even stronger than the heart rate (HR) traces. Spectrograms in the right column of FIG. 3 show that the frequency notching method according to certain embodiments is effective in removing motion traces, as the HR traces dominate after notching.

As also illustrated in FIG. 1, system 100 may also include a spectrogram based frequency estimation block 170 configured to output an estimate of the heart rate. In an embodiment, frequency estimation block 170 may include a robust frequency estimator for noisy face color signals from fitness exercises. Instead of directly finding the peak (the mode) of the power spectrum for every time bin that may result in a discontinuous estimated heart-rate signal, one embodiment may construct a two-step process to ensure the estimated signal is smooth. In an embodiment, a single most probable strap is selected from the spectrogram, and each time bin of the spectrogram image may be binarized per the 95th percentile of the power spectrum of that bin. An embodiment may then dilate and erode the image in order to connect the broken strap. The largest connected region may be found using a traverse algorithm such as the breadth-first search and is considered as the most probable strap.

Figure 4A:
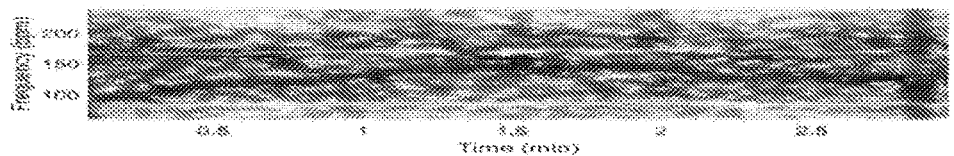
FIG. 4a illustrates an example of spectrogram results with a weakly connected frequency strap.
Figure 4B:
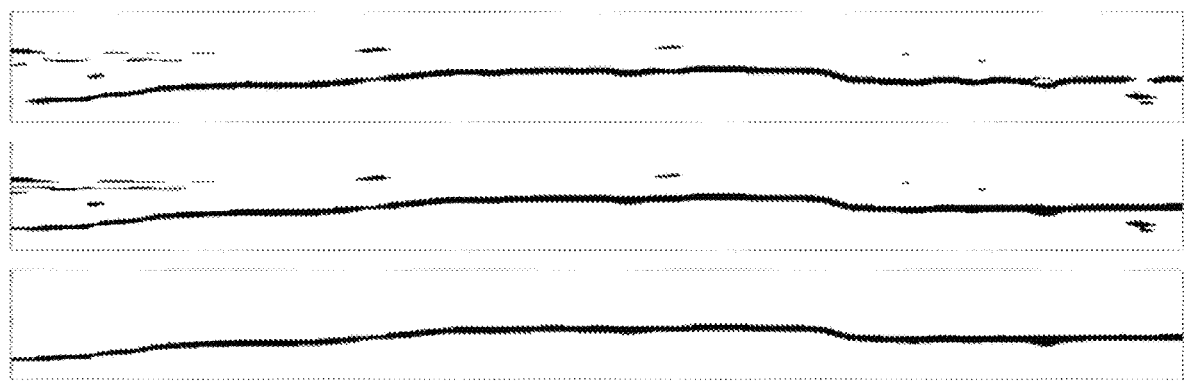
FIG. 4b illustrates an example of spectrogram results after the operations of binarization using, dilation and erosion, and small regions removal, according to certain embodiments.

FIG. 4 illustrates an example of spectrogram results according to the steps of FIG. 1. More specifically, FIG. 4a illustrates a spectrogram with a weakly connected frequency strap, and FIG. 4b illustrates the results after the operations of binarization using $95^{th}$ percentile, dilation and erosion, and small regions removal, according to certain embodiments.

An embodiment may then use a weighted frequency within the frequency range specified by the strap, $F_i$, as the frequency estimate for ith time bin. Denoting the frequency estimate as $\hat{f}_{HR}(i)$ according to the following:

$$\hat{f}_{HR}(i) = \sum_{f \in F_i} w_{i,f} * f$$

where $w_{i,f}=|S(i,f)|/\Sigma_{f \in F_i}|S(i,f)|$, and $S(i, :)$ is the power spectrum at the ith bin.

Thus, according to the example embodiment of FIG. 1, red green blue (RGB) weights may be used to resist unwanted illumination changes due to motion. The registration error may be minimized using pixel-level optical flow based motion compensation that is capable of generating almost "frozen" videos for best extracting the face color signals. De-trending may be used to remove the illumination variation caused by passersby and/or the gradual change of sunlight that can cause problems for frequency estimation. Notching operations may be applied to remove frequency traces caused by periodic motion of fitness exercises with the help of motion information from the face tracker and the optical flow. A robust spectrogram based frequency estimator may then be applied to extract the final heart rate trace.

Figure 5:
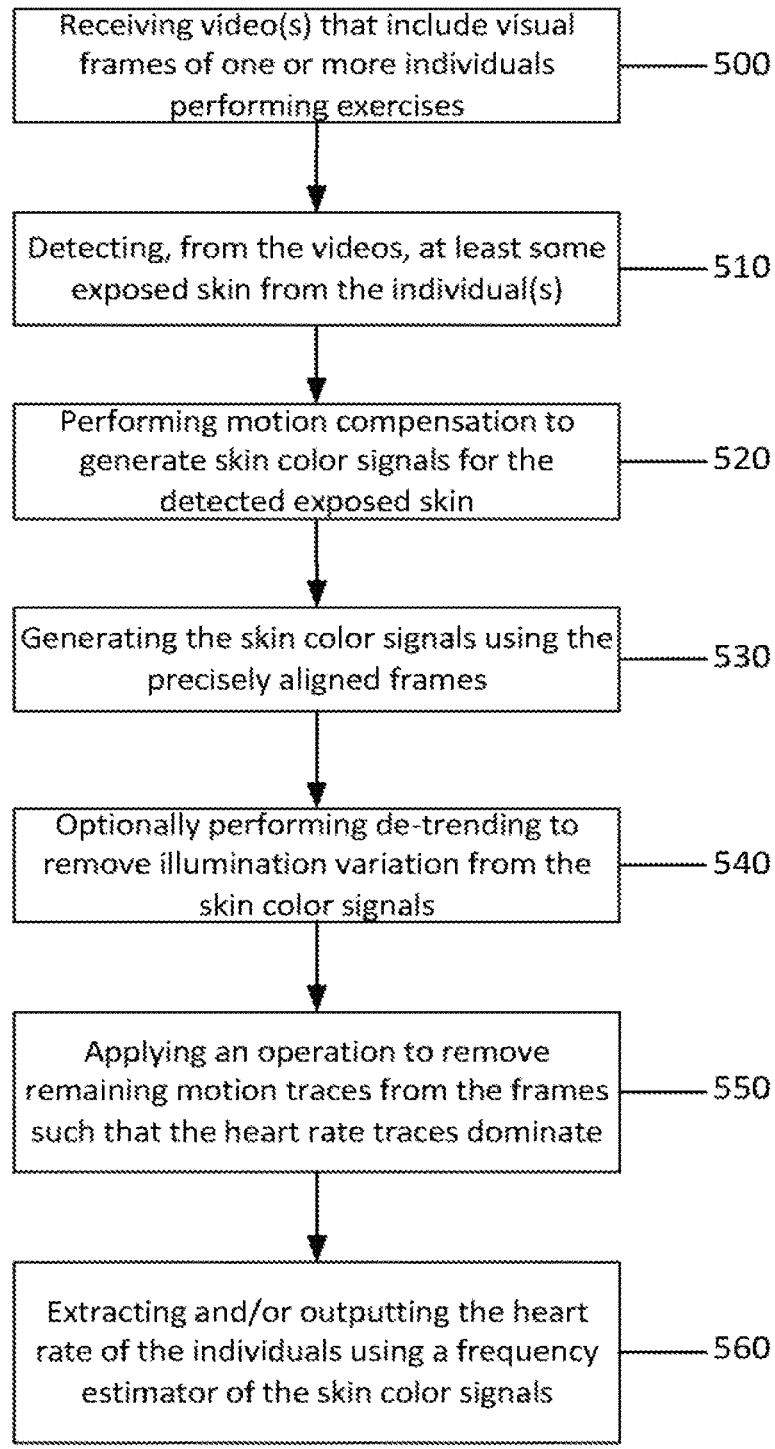
FIG. 5 illustrates an example flow diagram of a process for contactless measurement of heart rate, according to an example embodiment.

FIG. 5 illustrates an example flow diagram of a method or process for contactless measurement of heart rate, according to an example embodiment. In certain embodiments, the method of FIG. 5 may be performed by the system of FIG. 1 discussed above. As illustrated in the example of FIG. 5, the method may include, at 500, receiving or capturing one or more fitness or exercise videos that may include visual frames or images of one or more individuals performing exercises or other physical activity. According to certain embodiments, the method may then include, at 510, detecting at least some portion of exposed skin of the individual(s) in the video(s). In one embodiment, the exposed skin may include one or more face(s) of the individual(s) from the fitness videos.

In an embodiment, the method may also include, at 520, performing (pixel-level) motion compensation in order to generate skin color signals for the detected exposed skin. In an embodiment, the skin color signals may be face color signals. According to one embodiment, the performing of the motion compensation 520 may include performing optical flow based motion compensation for precisely aligning frames of the face(s). For example, in one embodiment, the performing of the optical flow based motion compensation may include executing an optical flow algorithm to find correspondences of all points on the face(s) between two frames of the video(s). In one example, optical flow uses gradient information to iteratively refine the estimated motion vector field. According to an embodiment, in order to avoid being trapped in local optima, the performing of the motion compensation 520 may include performing a pre-alignment step to bring the face images roughly aligned before conducting the optical flow based motion compensation to obtain the fine-grain alignment. In an example embodiment, the pre-alignment step may include utilizing a Viola-Jones face detector to obtain rough estimates of the location and size of the face(s), and clipping and resizing the face region of each frame to 180 pixels in height, in order to effectively generate a pre-aligned video for the face region. The pre-alignment step may significantly reduce the lengths of motion vectors, which in turn makes results of optical flow more reliable. In one example, two face images may be likely to have a global color difference due to the heartbeat. In order to conduct a precise face alignment, in one embodiment, the performing of the motion compensation 520 may include assuming that the intensity I of a point in two frames are related by an affine model, namely:

$$I(x + \Delta x, y + \Delta y, t+1) = (1 - \epsilon)I(x, y, t) + b \quad (1)$$

where $\epsilon$ and b control the scaling and bias of the intensities between two frames. Traditional techniques tackling the illumination consistency cases such as Taylor expansion and regularization can be similarly applied, according to certain embodiments.

According to certain embodiments, the performing of the motion compensation 520 may include dividing each video into small temporal segments with one frame overlapping for successive segments. In an embodiment, the frame in the middle of the segment may be used as the reference for optical flow based motion compensation. This would ensure that two frames being aligned do not have significant occlusion due to long separation in time.

Continuing with the example illustrated in FIG. 5, the method may further include, at 530, generating the skin color signals (or face color signals), for example, using the precisely aligned frames of the face(s) (produced from the motion compensation step 520). In an embodiment, the generating of the skin color signals 530 may include estimating a skin or face color for each frame by taking a spatial average over pixels of a cheek of the face(s) for the R, G, and B channels, respectively. According to some embodiments, the generating of the skin color signals 530 may include concatenating segments of the video(s) into color signals. When concatenating the segments, in an embodiment, the last point of the current segment and the first point of the next segment may have different intensities because they correspond to the same frame whose motion compensation were conducted with respect to two different references. Thus, according to an embodiment, the generating of the skin color signals 530 may include calculating the difference of the intensity between the two points and using the resulting value to bias the signal of the next segment in order to maintain the continuity. The skin or face color signals may contain color change due to the heartbeat, and illumination change due to face motions such as tilting. In an embodiment, the green channel may be used because it corresponds to the absorption peak of (oxy-) hemoglobin that changes periodically as the heartbeat, and source separation methods such as ICA may also be used to separate the heartbeat component. According to an embodiment, the generating of the skin color signals 530 may include using the fixed linear weights (-1,2,-1) for R, G, B channels to best retain the heartbeat component while compensating for the motion induced illumination change.

In an embodiment, the generating of the skin color signals 530 may further include determining the cheek regions of the face(s), or regions of other exposed skin, for conducting spatial averaging. In one example, the determining of the cheek regions may include constructing two conservative regions that do not contain facial structures and are most upfront in order to avoid strong motion-induced specular illumination changes. Certain embodiments may then use identified facial landmarks to facilitate the construction of the cheek regions. In one embodiment, each cheek region may be constructed to be a polygon that has a safe margin to the facial structures protected by the landmarks.

As further illustrated in the example of FIG. 5, in one embodiment, the method may also include, at 540, optionally performing de-trending to remove the illumination variation from the face color signals. It is noted that, in some embodiments, the de-trending may not need to be performed when there is little lighting variation. In an embodiment, the de-trending step 540 may take the skin or face color signal as an input and remove illumination variation. It is noted that illumination variation can be caused by passersby and/or the gradual change of sunlight, for example, which can result in the skin or face color signal to drift. According to one embodiment, the de-trending step 540 may include estimating the varying trend and then subtracting it from a raw face color signal, $x_{raw} \in R^L$, where L is the length of the signal. The trend may be assumed to be a clean, unknown version of $x_{raw}$ with a property that its accumulated convexity measured for every point on the signal is as small as possible, namely:

$$\hat{x}_{trend} = \underset{x}{\operatorname{argmax}} \|x_{raw} - x\|^2 + \lambda \|D_2 x\|^2 \qquad (2)$$

where $\lambda$ is a regularization parameter controlling the smoothness of the estimated trend, and $D_2 \in R^{L \times L}$ is a spare toeplitz second-order difference matrix. The closed-form solution is $\hat{x}_{trend} = (I + \lambda D_2^T D_2)^{-1} x_{raw}$. Hence, the detrended signal is $x_{raw} - \hat{x}_{trend}$. After the de-trending step 540, an embodiment may use a bandpass filter to reject the frequency components that are outside a normal range of human heart rate.

As also illustrated in the example of FIG. 5, in an embodiment, the method may further include, at 550, applying an operation to remove remaining motion traces from the frames such that the heart rate traces dominate. According to one embodiment, the operation to remove motion traces may include a motion frequency notching operation and/or an adaptive filtering operation. In an embodiment, a motion frequency notching operation may include combining motion information from the face tracker and the optical flow to generate two time signals, one for the x-direction and the other for the y-direction. For each time bin on the spectrogram, one embodiment may conduct two notch operations based on the dominating frequency estimated from the x- and y-motion components.

In an embodiment, the method may then include, at 560, extracting and/or outputting the heart rate of the individual(s) from the video(s) using a frequency estimator for the face color signals. According to one example embodiment, the frequency estimator may be a spectrogram based frequency estimator. In an embodiment, the extracting 560 may include using a robust frequency estimator for noisy face color signals from fitness exercises. Instead of directly finding the peak (the mode) of the power spectrum for every time bin that may result in a discontinuous estimated heart-rate signal, the extracting 560 may include constructing a two-step process to ensure the estimated signal is smooth. In an embodiment, a single most probable strap is selected from the spectrogram, and each time bin of the spectrogram image may be binarized per the 95th percentile of the power spectrum of that bin. An embodiment may then dilate and erode the image in order to connect the broken strap. The largest connected region may be found using a traverse algorithm such as the breadth-first search and is considered as the most probable strap. It is noted that the spectrogram based frequency estimation described above is just one tracking approach, according to some embodiments; other embodiments can work with other tracking techniques that can handle weak and noisy traces.

Figure 6:
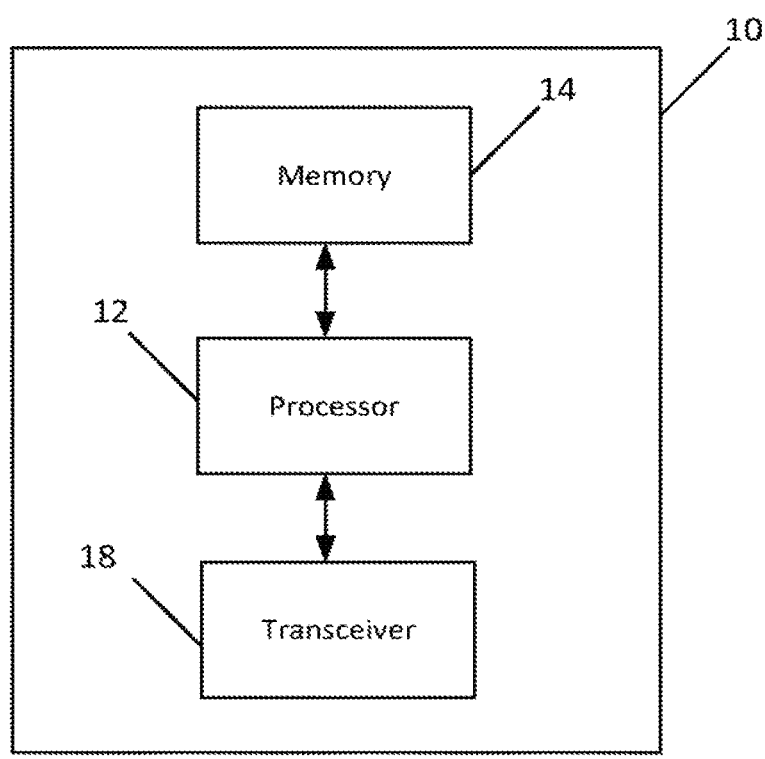
FIG. 6 illustrates an example block diagram of an apparatus, according to an embodiment.

FIG. 6 illustrates an example of an apparatus 10 according to one embodiment. In an example embodiment, apparatus 10 may include a server, computer, or other device capable of executing arithmetic or logical operations. It should be noted that one skilled in the art would understand that apparatus 10 may include components or features not shown in FIG. 6.

As illustrated in the example of FIG. 6, apparatus 10 may include a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. In further example embodiments, processor 12 may include a specialized processor or a ML/data analytics based application processor, such as a graphics processing unit (GPU) or tensor processing unit (TPU). In yet a further example, processor 12 may include a neural network or long short term memory (LSTM) architecture or hardware, etc.

While a single processor 12 is shown in FIG. 6, multiple processors may be utilized according to other example embodiments. For example, it should be understood that, in certain example embodiments, apparatus 10 may include two or more processors that may form a multiprocessor system (e.g., in this case processor 12 may represent a multiprocessor) that may support multiprocessing. In certain example embodiments, the multiprocessor system may be tightly coupled or loosely coupled (e.g., to form a computer cluster).

Processor 12 may perform functions associated with the operation of apparatus 10, which may include, for example, executing the process illustrated in the example of FIG. 5.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read only memory (ROM), static storage such as a magnetic or optical disk, hard disk drive (HDD), or any other type of non-transitory machine or computer readable media. The instructions stored in memory 14 may include program instructions or computer program code that, when executed by processor 12, enable the apparatus 10 to perform tasks as described herein. In an embodiment, memory 14 may store modules corresponding to the blocks 110, 120, 130, 140, 150, 160, 170 illustrated in the example of FIG. 1, or corresponding to blocks 710, 715, 720, 725, 730, 735, 740 illustrated in the example of FIG. 7.

In an example embodiment, apparatus 10 may further include or be coupled to (internal or external) a drive or port that is configured to accept and read an external computer readable storage medium, such as an optical disc, USB drive, flash drive, or any other storage medium. For example, the external computer readable storage medium may store a computer program or software for execution by processor 12 and/or apparatus 10.

In some example embodiments, apparatus 10 may further include or be coupled to a transceiver 18 configured to transmit and receive information. Additionally or alternatively, in some example embodiments, apparatus 10 may include an input and/or output device (I/O device).

In an example embodiment, memory 14 may store software modules that provide functionality when executed by processor 12. The modules may include, for example, an operating system that provides operating system functionality for apparatus 10. According to certain embodiments, the modules may include a face detection module, motion estimation module, cheek regions selection module, spatial averaging module, de-trending and temporal filtering module, motion frequency notching module, and/or spectrogram based frequency estimation module. The memory may also store one or more functional modules, such as an application or program, to provide additional functionality for apparatus 10. The components of apparatus 10 may be implemented in hardware, or as any suitable combination of hardware and software.

According to some example embodiments, processor 12 and memory 14 may be included in or may form a part of processing circuitry or control circuitry. In addition, in some example embodiments, transceiver 18 may be included in or may form a part of transceiving circuitry.

As introduced above, in example embodiments, apparatus 10 may be a computer, server, or other similar device. According to example embodiments, apparatus 10 may be controlled by memory 14 and processor 12 to perform the functions associated with any of the example embodiments described herein, such as the system or signaling flow diagrams illustrated in FIGS. 1 and 5. For example, in certain embodiments, apparatus 10 may be controlled by memory 14 and processor 12 to perform one or more of the steps illustrated in FIG. 5. In example embodiments, for instance, apparatus 10 may be configured to perform a process for contactless measurement of heart rates according to the system illustrated in FIG. 1. In further embodiments, apparatus 10 may be configured to perform a process for contactless measurement of PR and/or PRV according to the system illustrated in FIG. 7 discussed below.

To recapture the challenges of rPPG sensing discussed above, the challenges can arise from each component of the sensing system, namely, the camera, the illumination conditions, and the subject. In a fitness scenario, the motion-induced intensity and color change may dominate over the reflected light from the facial skin, while the pulse-induced color variation is subtle. The measurement is also associated with a group of nuisance signals, such as sensor noise and quantization noise. To extract the subtle pulse signal that may have a much smaller magnitude than the dominating signal components and simultaneously protect it from being corrupted by other nuisance signals, the problem should be approached with extra caution.

Figure 7:
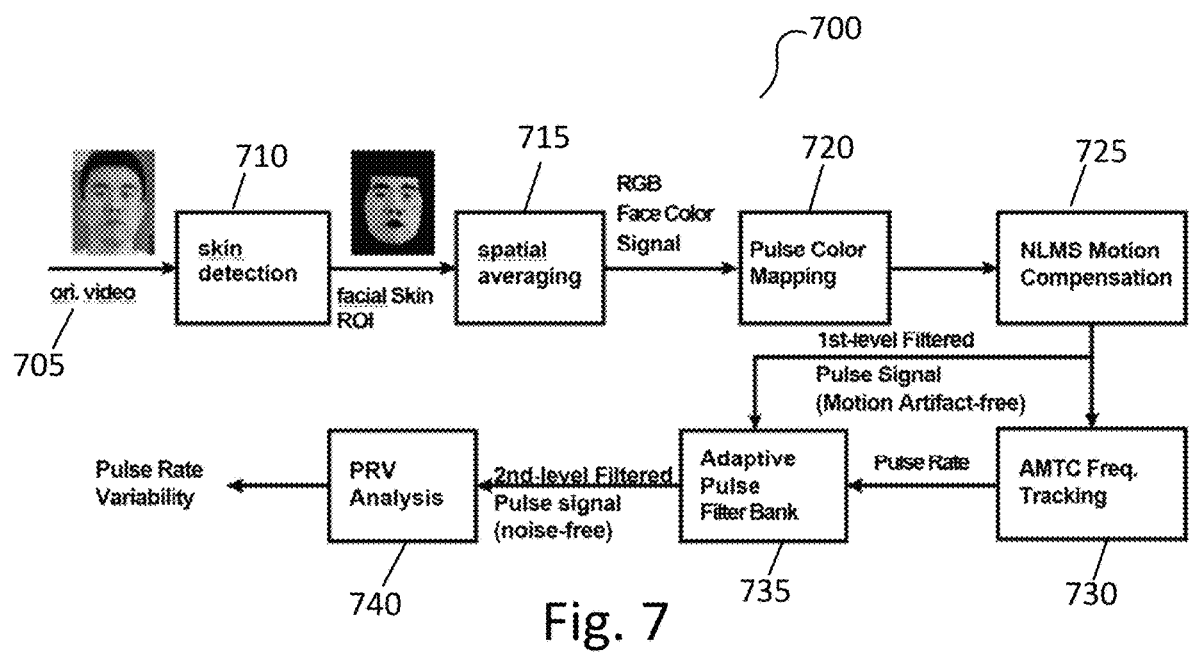
FIG. 7 illustrates an example remote photoplethysmography (rPPG) system, according to an embodiment.

In an embodiment of the present disclosure, an rPPG system for robust estimation during fitness exercise of heart rate (HR) or pulse rate (PR) and interbeat interval (IBI) signal is provided, whereby the IBI signal can support the estimation of heart/pulse rate variability (HRV/PRV). FIG. 7 illustrates an example rPPG system 700, according to certain embodiments. In an embodiment, the system 700 may take one or more videos 705 as an input. As introduced above, the video(s) 705 may include fitness or exercise videos, one or more facial images, or images of other exposed skin, of a person.

As illustrated in the example of FIG. 7, system 700 may include a skin detection block 710 configured to detect exposed skin from the input video(s) 705. In an embodiment, the skin detection block 710 may include a new unsupervised learning scheme to detect the skin pixels on a face accurately. According to an embodiment, in the skin detection block 710, an ellipsoid-shaped skin classifier may be learned from the face pixel colors in the first few frames of the video 705 and may be deployed in the subsequent frames to detect facial skins. This step enhances the quality of the extracted pulse signal as the skin surface contains the highest pulse signal-to-noise ratio (SNR).

In an embodiment, the system 700 may also include a spatial averaging block 715 configured to spatially average the three color channels in red, green, and blue inside the detected facial skin region, to produce a RGB face color signal. A pulse color mapping block 720 may be configured to map the face color temporal measurement to a color direction that generates the highest pulse SNR. A normalized least mean square filter 725 is then adopted to mitigate the motion artifacts in the preprocessed pulse signal. A frequency trace tracking algorithm implemented in an Adaptive Multi-Trace Carving (AMTC) frequency tracking block 730 is configured to track the PR accurately even when the pulse SNR is extremely low. A filter bank 735 with an adaptive subband modification layer is configured for precise bandpass operation to reconstruct the pulse signal in the time domain and facilitate the estimation of the PRV. The second level filtered pulse signal produced by the filter bank 735 can be provided to a PRV analysis block 740, which is configured to output the estimated PRV. Certain embodiments can also address additional issues closely supporting the PR and PRV estimation, such as the privacy protection of video data containing simultaneously the sensitive identity and physiological information.

Certain embodiments can provide a highly precise motion compensation in order to generate a clean face color signal. For example, in an embodiment, the skin detection block 710, as depicted in the example of FIG. 7, may include a DNN face detector trained with a Single-Shot-Multibox detector (SSD) and a ResNet framework to obtain a rectangular face detection region. The SSD-ResNet can provide a better detection result compared with traditional methods, such as the Viola-Jones detector, especially for face profiles. In an embodiment, a CSR-DCF algorithm may be used to track the face region. A facial region of interest (ROI) may be located with the facial landmarks estimated with an ensemble of regression trees. Certain embodiments may then follow a ROI selection process to include the cheek and forehead regions of a face.

Figure 8:
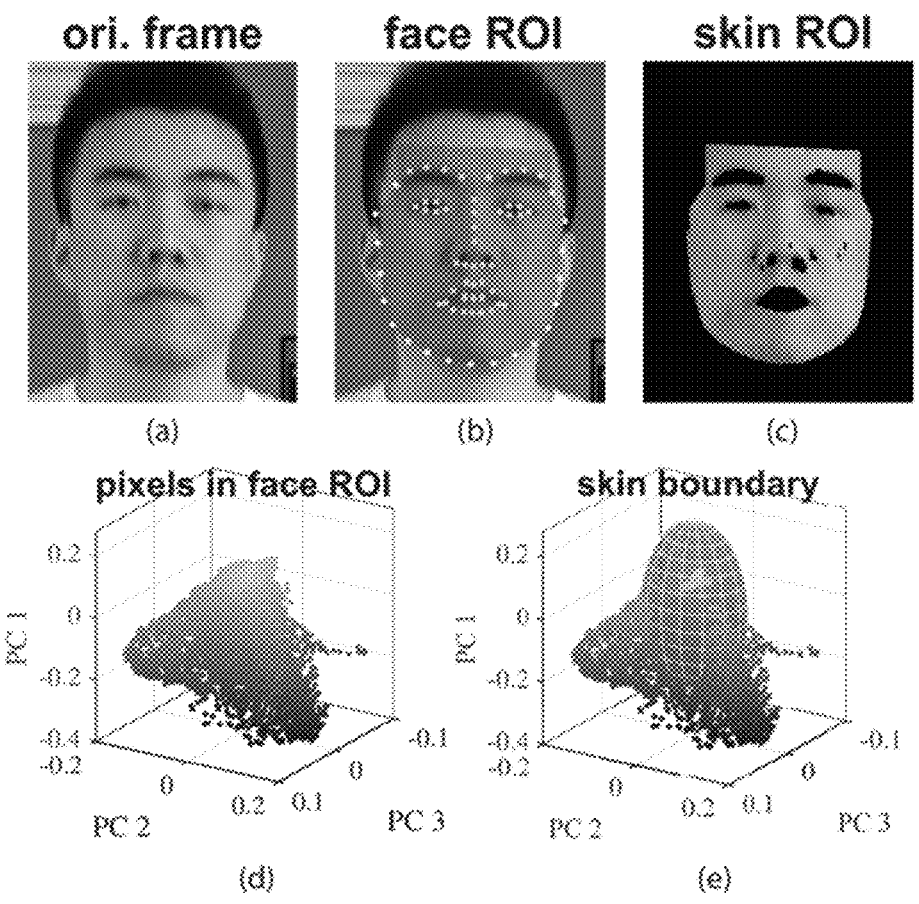
FIG. 8(a) illustrates a face landmark localization and skin classification result example, according to an embodiment.
FIG. 8(b) illustrates a face landmark localization and skin classification result example, according to an embodiment.
FIG. 8(c) illustrates an example of detected skin pixels, according to an embodiment.
FIG. 8(d) illustrates an example scatter plot of skin pixels, according to an embodiment.
FIG. 8(e) illustrates an example of the scatter plot overlaid with a boundary of a skin classifier, according to an embodiment.

FIG. 8 illustrates a face landmark localization and skin classification result example. FIG. 8(*a*) depicts an example cropped video frame, and FIG. 8(*b*) depicts facial landmark localization result (dots) and the estimated face ROI (the transparent area). FIG. 8(*d*) illustrates a scatter plot of the skin pixels in face ROI in their top three dominating principle component directions according to eigenvectors of S. The dots' color is consistent with its original color in the frame. The scatter plot is overlaid with the boundary of the skin classifier in FIG. 8(*e*). In FIG. 8(*c*), the corresponding detected skin pixels (in their original color) are depicted according to the classifier shown in FIG. 8(*e*).

Certain embodiments may be configured to perform skin tone learning and pruning. The non-skin regions on the face (such as eyebrows, nostril, forehead hair, and glasses) as well as the regions dominated by the specular reflections has little or no contribution to the pulse signal extraction, and the possible non-rigid motion in mouth region (e.g., the talking motion) or in eye region (e.g., blinking) add additional distortions to the rPPG signal. Thus, a rPPG system according to certain embodiments is configured to first reject those non-skin pixels in the facial ROI before any pulse extraction.

However, skin detection can be challenging due to the fact that the skin color is affected by both explicit and implicit factors, such as the variation of the light spectrum, the spectrum response of the camera, and the subject-wise skin tone differences due to the difference in the density distribution of melanin in the skin layer. The direct use of a pre-trained skin detection model may generate high false positive skin detection results, when the model accounts for all possible skin-tone variations, while high false negative results in a test instance, when the model fails to include the specific skin color. To address this problem, certain embodiments include a hypothesis testing scheme to detect skin pixels based on a scenario-tailored learning of the probability distribution of the skin pixels, which is detailed below.

Certain embodiments are configured to learn the probability distribution of a subject's skin pixel based on the colors of pixels collected from the facial ROI in the first few frames of a video. Assuming the time-invariance of a person's intrinsic skin color and the surrounding illumination condition, some embodiments provide a skin detection method that is based on the learned parameters and the a posteriori (MAP) rule. Enlightened by the color space selection schemes optimized for skin detection, the pixel samples may be mapped to the color space (R-G, R-B, Y-Cr, H), where H denotes the hue channel. Given a pixel random variable $s \in R^{4 \times 1}$ in the color space from the face ROI, the following hypotheses are made:

Hypothesis $H_0$: s is a skin pixel,

Hypothesis $H_1$: s is a non-skin pixel, assuming the a priori probabilities for the two hypotheses are $P(H_0)=p_0$ and $P(H_1)=1-p_0$, respectively. To capture the spatial variation of a subject's skin color on their face, the conditional distribution of s under $H_0$ may be modeled as a multivariate Gaussian distribution parameterized by the mean $\mu_s$ and covariance matrix $\Sigma$.

In an embodiment, the density function of s under H0 may be written as:

$$f_{s|H}(s_1 \mid H_0) = \frac{1}{\sqrt{(2\pi)^4 |\Sigma|}} \exp\left(-\frac{1}{2}(s_i - \mu_s)^T \sum\nolimits^{-1} (s_i - \mu_s)\right) \quad (3)$$

According to certain embodiments, the conditional distribution of s under $H_1$ may be modeled as a uniform distribution assuming that a non-skin pixel in the scene is equally likely to be any specific color. Then, the density function of s under $H_1$ is:

$$f_{s|H}(s_i \mid H_1) = \alpha, \quad (4)$$

where $\alpha$ is the model parameter satisfying the unitary rule of probability.

According to the MAP rule, the decision may be specified as:

$$P(H_1 \mid s = s_i) \underset{H_0}{\overset{H_1}{\gtreqless}} P(H_0 \mid s = s_i), \quad (5)$$

which leads to the log likelihood ratio test as:

$$\log\left(\frac{f_{s|H}(s_i H_1)}{f_{s|H}(s_i \mid H_0)}\right) \underset{H_0}{\overset{H_1}{\gtreqless}} \log\left(\frac{p_0}{p_1}\right) \quad (6)$$

Substituting the conditional density functions (3) and (4) into (6), results in:

$$(s_i - \mu_s)^T \sum\nolimits^{-1} (s_i - \mu_s) \underset{H_0}{\overset{H_1}{\gtreqless}} \phi, \quad (7)$$

where $\varphi = 2 \log p_0 - 2 \log((2\pi)^2(1-p_0)\alpha\sqrt{|\Sigma|})$. It can be observed from (7) that the skin detection boundary is defined by a hyperellipsoid shaped isodensity surface centered at si. The decision rule for the skin detection may be based on the statistical modeling of both the skin pixels and non-skin pixels. Next, the estimation of the skin color model parameters $\mu_s$ and $\Sigma$ may be performed.

Letting $S \in R^{4 \times N}$ denote a sample pixel matrix for the face ROI, the learning objective includes to estimate the skin model parameters $\mu_s$ and $\Sigma$ from S. The direct use of the maximum likelihood estimator, i.e., the data mean and the data variance to estimate $\mu_s$ and $\Sigma$ generates biases. This is because the non-skin pixels in the sample collection S do not satisfy the same distribution with the skin pixels.

In certain embodiments, to address this problem and exclude the negative effect from the non-skin pixels, the model parameters may be estimated by iteratively excluding out a small amount of non-skin pixels. For example, in each iteration, $\mu_s$ and $\Sigma$ may be estimated using the sample mean and sample covariance matrix. The conditional density values may then be computed according to (3) for each sample and 5% of the sample points with the least probability values may be discarded. After several iterations, the non-skin pixels will all be discarded and the estimates become unbiased. The success of the exclusion of the non-skin pixels is based on the fact that most of the samples in the facial regions are skin pixels, and the initial estimate of $\mu_s$ will be closer to the cluster of the skin pixels rather than sparsely-distributed non-skin pixels.

In FIG. 8 discussed above, one example of the parameter learning and the skin detection result is illustrated. $\Sigma$ may be represented via its eigen structure as $\Sigma = EVE^\tau$, where $V \in R^{4 \times 4}$ is a diagonal matrix with the descending diagonal entries as the eigenvalues of $\Sigma$, and E is a unitary matrix with each column as a eigenvector of $\Sigma$. We name the new random variables $s\sim$ defined to be $(s-\mu_s)^\tau E$ as the principal components of s. In FIG. 8(d), the pixel samples are displayed in terms of the first three components of $s\sim$ for better visualization. It is noted that the principal components are mutually independent based on the property of the multivariate Gaussian distribution, and the eigenvectors in E represent the principal axes of the ellipsoid $\{\xi \in R^4 | (s_i-\xi)^\tau \Sigma^{-1}(s_i-\xi)=\varphi\}$, which is shown in FIG. 8(d) as transparent layer over the face. The final skin detection result in face ROI is visualized in FIG. 8(c). It is noted that the detection process according to certain embodiments retains most of the skin pixels and successfully rejects most of the non-skin pixels and the pixels that are dominated by the specular reflection.

Some embodiments include advanced learning to adapt rPPG signal extraction to various skin colors. For different skin colors, the percentage of reflected light and color spectrum of the light reflection process are different. Complementing the improved skin detection discussed above, certain embodiments provide a new, targeted learning-based approach to learn the best nonlinear function that fuses three color channels into a PPG signal while rejecting the motion noise. In an embodiment, a recurrent neural network (RNN) with long short-term memory (LSTM) units can be adopted to map a sequence of facial images (which contain the skin regions only) to a label signal. In this scenario, the LSTM-based RNN serves as a nonlinear aggregator and robust de-noiser. The resulting RNN-predicted PPG signal can then be used for heart rate and respiration tracking. Compared to an end-to-end neural network approach, the need of training data of this principled approach (which applies data-driven learning to the critical module) is substantially smaller and manageable based on the currently available datasets, and the overall results are explainable. In certain embodiments, this principled learning framework can also output a confidence score based on the estimated facial pulse SNR, to provide a quantitative reliability of the respiration pattern and heart rate.

Certain embodiments include motion compensation via multi-channel adaptive processing. In this aspect, once the skin pixels are detected in each frame, a temporal RGB sequence $\tilde{C}(t)$ may be generated by spatially averaging the RGB values of the detected skin pixels and temporally normalized in each color channel. $\tilde{C}(t)$ may then be linearly mapped to a specific color direction in the RGB space to generate a 1-D pulse signal. Without loss of generality, it may be assumed that the face color signal $\tilde{C}(t)$ may be mapped to the POS direction, which is one of the most robust color features representing the highest relative pulse strength. The projected 1-D processed signal may be denoted as $c_{pos}(t)$, as follows:

$$c_{pos}(t) = p^T \tilde{C}(t) = \overbrace{p^T u'_p \cdot p(t)}^{Pulse} + \overbrace{\sum_{k=1}^{K} p^T u_{m,k} \cdot m_k(t)}^{Motion\ Residue}, \quad (8)$$

where $p \in R^{3 \times 1}$ denotes the projection vector of the POS algorithm, $u_p$ denotes the unit color direction of the pulse component, and um,k denotes the unit color direction of the kth motion component. The motion residue term in Eq. (8) is negligible when the illumination source is single, as the POS direction is orthogonal to the color direction of the motion-induced intensity change, and the specular change is suppressed via "alpha tuning". However, if the video is captured in an uncontrolled environment, the motion residue term is often non-negligible, and sometimes can be more significant than the pulse term.

Figure 9:
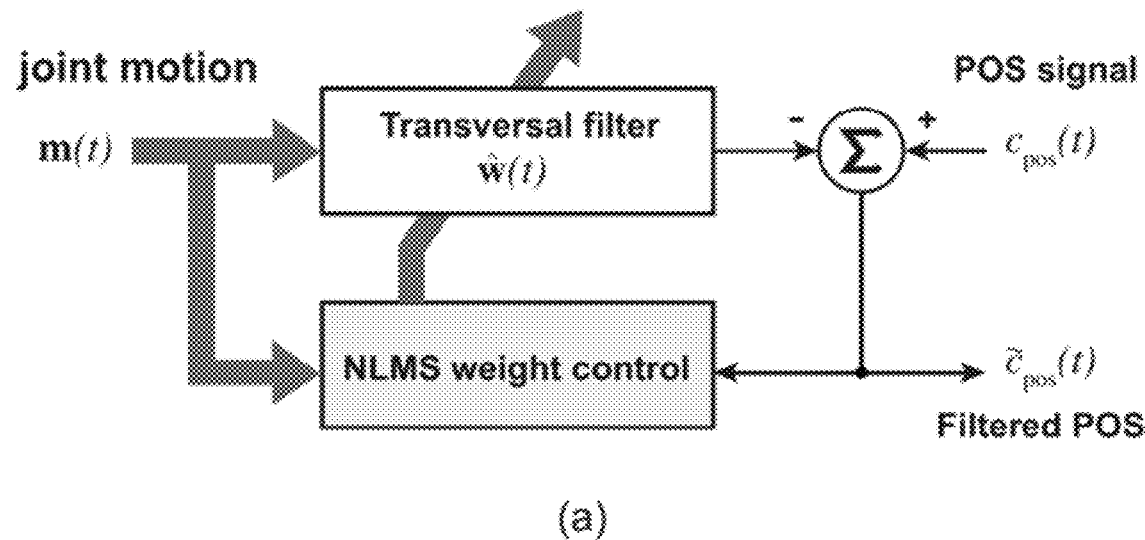
FIG. 9(a) illustrates an example of the structure of a motion compensation filter framework, according to certain embodiments.
FIG. 9(b) illustrates an example of the structure of a motion compensation filter framework, according to another embodiment.
Figure 9:
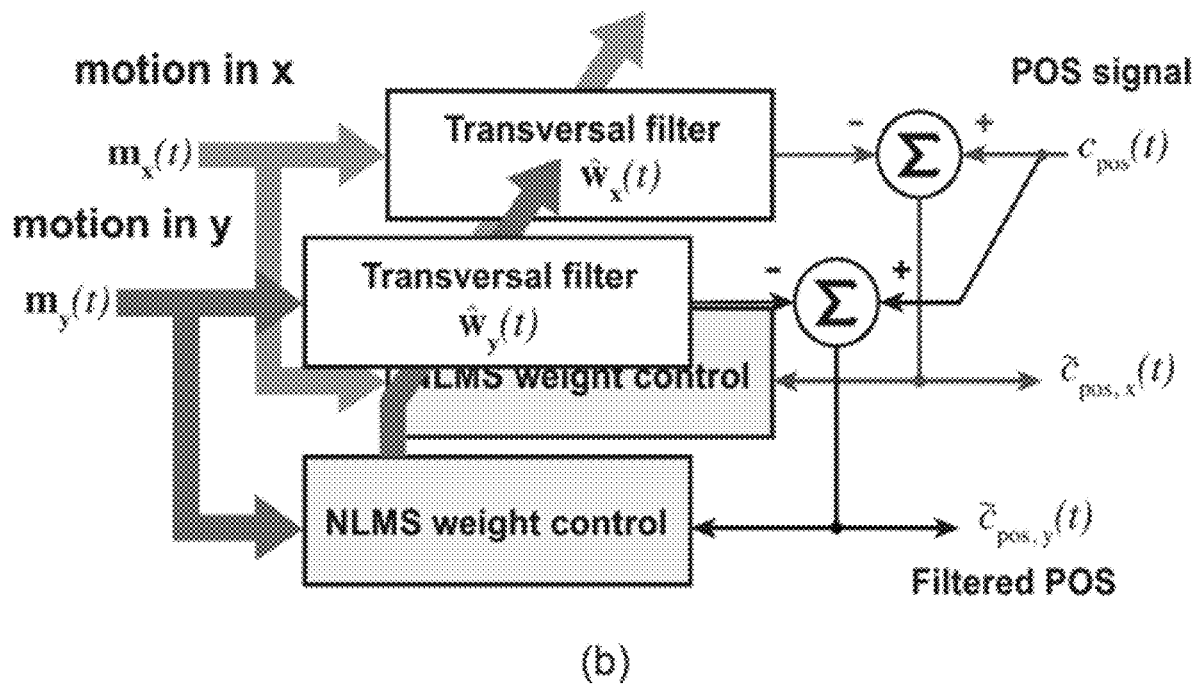

In an embodiment, to address this problem, the motion term in (8) may be estimated using the estimate of the face motion in both horizontal and vertical directions. It is noted that the subject motion and the motion artifact in rPPG signal share the causal relation and are thus highly correlated. Meanwhile, it may be assumed that the pulse signal is uncorrelated with the subject motion. To capture this signal correlation, an embodiment may use the Normalized Least Mean Square (NLMS) filter, and the face motion signals in both horizontal and vertical directions may be estimated and used to approximate and mitigate the motion residue term in (8). The estimated face motion sequence in horizontal and vertical directions may be denoted as $m_x(t)$ and $m_y(t)$. FIG. 9 illustrates two examples of the structure of a motion compensation filter framework, according to certain embodiments. More specifically, FIG. 9(a) illustrates a NLMS-1CH framework, and FIG. 9(b) illustrates a NLMS-2CH framework.

In the first scheme, $c_{pos}(t)$ is treated as the filter's desired response at time instance t. The motion tap vector $m^\tau(t)$ is defined as $[m_x(t-M+1), m_x(t-M+2), \ldots, m_x(t), m_y(t-M+1), m_y(t-M+2), \ldots, m_y(t)]$ as the input and $\tilde{c}_{pos}$ as the output of the system and also the error signal. The estimated tap-weight vector of the transversal filter is denoted as $\hat{w}(t)$, and weight control mechanism follows the NLMS algorithm as below:

$$\tilde{c}_{pos} = c_{pos} - \hat{w}^T(t)m(t), \quad (9)$$

$$\hat{w}(t+1) = \hat{w}(t) + \frac{\mu}{\|m(t)\|^2} m(t) \cdot \tilde{c}_{pos}, \quad (10)$$

where $\mu$ denotes the adaptation constant, which is normalized by the norm square of the input vector m(t).

The motion tap vector m(t) is highly correlated with the motion residue term $\Sigma_{k=1}^{K} \tau$ um, k·mk(t). Considering this correlation might be time variant, the NLMS weight control mechanism can be designed to track the system change. The adaptation is not limited to NLMS and can be generalized to incorporate other techniques based on the available computation and speed/resource constraints.

Certain embodiments provide pulse rate tracking via AMTC. To this end, in certain embodiments, the signal quality is improved via precise face tracking, skin detection, pulse color mapping, and adaptive motion filtering. It is noted that for a healthy human being, two consecutive heart/pulse rate measurements may not deviate too much from each other. Some embodiments may exploit this heart rate continuity property, and track people's heart rate by searching for the dominating frequency trace appearing in the signal's spectrogram image. An embodiment may utilize an AMTC framework to track the frequency. The process of the tracking algorithm is described below.

In an embodiment, $Z \in R_+^{M \times N}$ denotes the magnitude of a processed signal spectrogram image, which has N discretized bins along the time axis and M bins along the frequency axis. An embodiment can model the change of the frequency value between two consecutive bins at n−1 and n as a one step discrete-time Markov chain, characterized by a transition probability matrix $P \in R^{M \times M}$, where Pm'm=P(f(n)=m|f(n−1)=m'), $\forall$m, m'=1, . . . , M, and $\forall$n=2, . . . , N. The regularized single trace frequency tracking problem is formulated as follows:

$$f^* = \underset{f}{\operatorname{argmax}} \ E(f) + \lambda P(f), \quad (11)$$

In an embodiment, the regularized tracking problem in (11) can be solved efficiently via dynamic programming. First, an accumulated regularized maximum energy map $G \in R_+^{N \times M}$ may be iteratively computed column by column for all entries (m,n) as follows:

$$G(m, n) = Z(m, n) + \max_{m'=1,\ldots,M} \{G(m', n-1) + \lambda \log P_{m'm}\} \quad (12)$$

After completing the calculation at column n=N, the maximum value of the Nth column is denoted as f*(N). Second, in an embodiment, the optimal solution may be found by backtracking from the maximum entry of the last column of the accumulated map G. Specifically, an embodiment may iterate n from N−1 to 1 to solve for f*(n) as follows:

$$f^*(n) = \underset{f(n)}{\operatorname{argmax}} \quad (f(n), n) + \lambda \log P_{f(n)f^*(n+1)} \tag{13}$$

Figure 10:
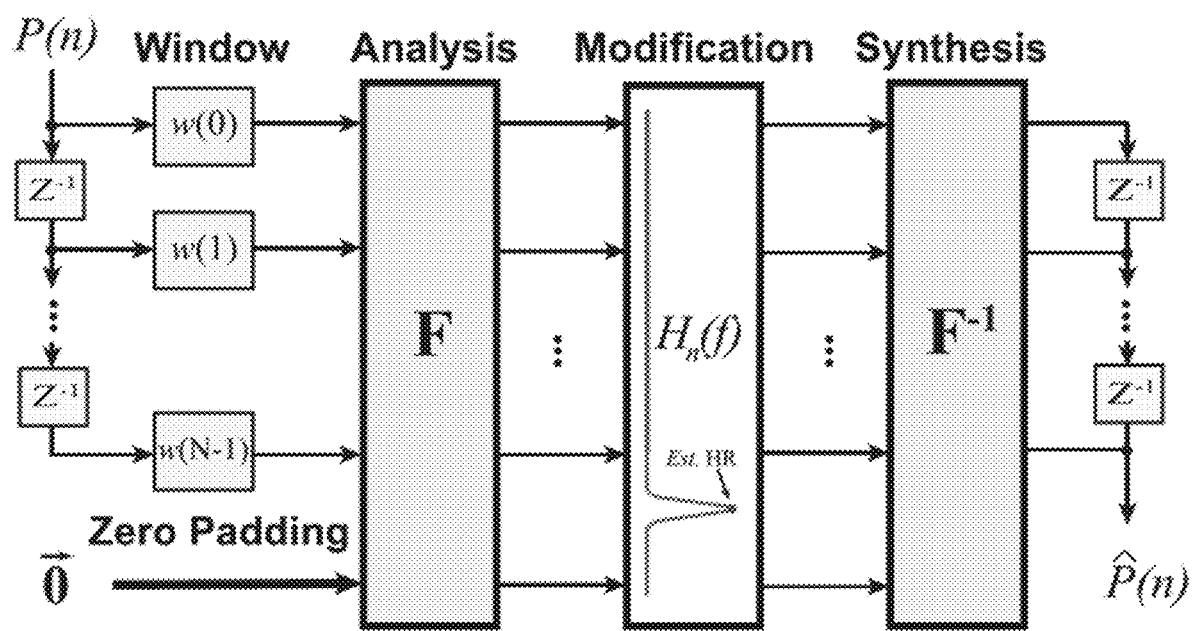
FIG. 10 illustrates an example filter bank system, according to an embodiment.

The analysis of the PRV may require a clean pulse signal so that certain recurrent cycle features, for example systolic peaks, are distinguishable over time to be able to estimate the interbeat intervals. According to an embodiment, the heart rate estimates may be exploited to precisely filter out all possible noise and interference existing in the processed pulse signal in a perfect reconstruction filter bank framework. FIG. 10 illustrates an example filter bank system, according to an embodiment. The processed 1-D pulse signal is P(n). At the time instance n, the mth (m=0, . . . , M−1) subband response is:

$$P_n(m) = \sum_{\tau=n-(N-1)}^{n} w(n-\tau) p(\tau) e^{-j2\pi m(\tau-M+1)/M} \tag{14}$$

where w(n) denotes a causal Hamming window, i.e.:

$$w(n) = \begin{cases} 0.54 - 0.46\cos(2\pi n/N), & 0 \le n \le N-1, \\ 0, & \text{otherwise.} \end{cases} \tag{15}$$

It is noted that in Eq. (14) and in FIG. 10, a sequence of zeros is padded at the end of the windowed time sequence $p_n(T)=p(T)w(n-T)$ to increase the number of subbands. The number of appended zeros, and thus the DFT length M should be large enough to accommodate the precise spectrum modification which is to be made. Note that the zeros padding operation does not bring additional information to the system, and the perfect reconstruction property is maintained.

To achieve the precise bandpass filtering goal, an embodiment may add a spectrum modification layer in between the analysis and the synthesis filter bank to suppress the noise outside the pulse rate frequency range. The modification process is guided by the current heart rate estimate so that the adaptive system can utilize the heart rate information to precisely reject the noise that is outside heart rate range. The modification is described as follows:

$$P'_n(m) = P_n(m) \cdot H_n(m), \quad m = 0, \ldots, M-1, \tag{16}$$

where $$H_n(m) = \alpha_n \cdot \exp\left(\frac{f_s \cdot m/M - f_{hr}(n)}{\sigma}\right)^2,$$

$f_s$ denotes the frame rate, $f_{hr}(n)$ denotes the current pulse rate estimates, $\sigma$ is a constant that controls the shape of the function $H_n(m)$, and $\alpha_n$ is a normalization parameter which is selected such that $\Sigma_{m=0}^{M-1} H_n(m)=1$. For a fixed value of n, $P_n(m)$ can be viewed as the normal discrete Fourier transform of the modified sequence $p_n(T)$. The synthesis rule follows as $p(t)=\Sigma_{m=0}^{M-1} P'_n(m) * e^{j2\pi m(t-M+1)/M}$.

Figure 11:
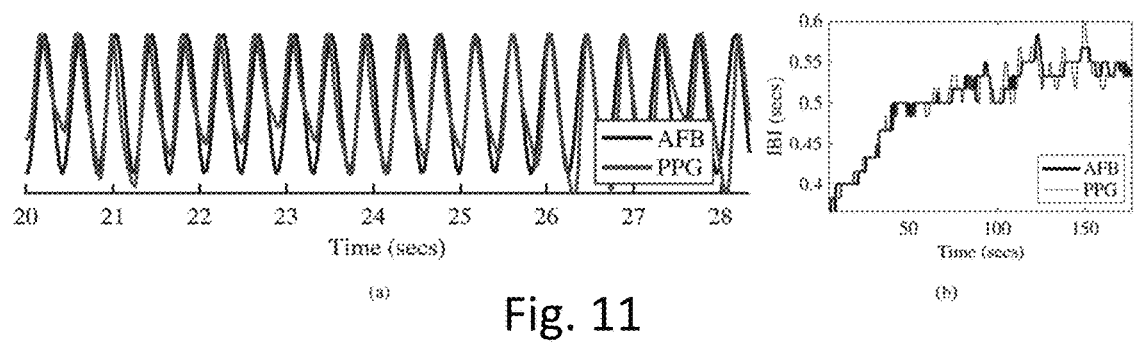
FIG. 11(a) illustrates an example of a filter pulse signal (AFB) after the second-level adaptive filtering process and the reference fingertip PPG signal, according to one example.
FIG. 11(b) depicts an example of the instantaneous inter beat intervals (IBI) estimated from the filtered rPPG signal versus the ones estimated from the finger-tip PPG signal, according to one example.

FIG. 11(a) illustrates an example of a filter pulse signal (AFB) after the second-level adaptive filtering process and the reference fingertip PPG signal. The upper envelopes of both signals have been adjusted for better visualization of the signal cycles. FIG. 11(b) depicts an example of the instantaneous inter beat intervals (IBI) estimated from the filtered rPPG signal versus the ones estimated from the finger-tip PPG signal. Therefore, FIG. 11(a) illustrates one example of the filtered pulse signal as the final output of the rPPG system. It should be noted that the signal is now highly cleaned, and that the systolic peaks of the filter pulse signal are almost aligned with the ones of the reference signal. This observation is consistent with the results shown in FIG. 11(b) that the IBI estimated from the rPPG signal is almost identical to that from the reference PPG signal. It should also be noted that, according to certain embodiments, there are numerous other choices of the analysis and synthesis modules as well as the modification that can be employed beyond the illustrated example of the DFT filterbank and subband modification in FIG. 10. The choices, such as linear vs. nonlinear, orthogonal vs. biorthogonal vs. overcomplete, fixed vs. adaptive vs. dictionary/learning based, can be compared and optimized depending on the imperfections to be suppressed and the useful signal aspects (such as pulse/heartbeat information) to be extracted, according to certain embodiments.

Collaborative data collection and benchmarking have played many important roles in advancing data-driven machine learning and data analytic applications. For video-based physiological monitoring, however, the face video data is often very sensitive in terms of the privacy of the persons being recorded and has a high concern of being misused, which discourages healthy sharing of data by the community to foster the advancement of this area. This has been a major hurdle to foster inter-organizational collaborations and benchmarking to advance the field. Certain embodiments therefore provide a novel anonymization transform that removes sensitive visual information identifying an individual, and at the same time, preserves the subtle color and movement changes that contain relevant physiological information so that different core algorithms can be compared on the same ground over a large data collection contributed from different sources, and synergistic improvement can be made.

Figure 12:
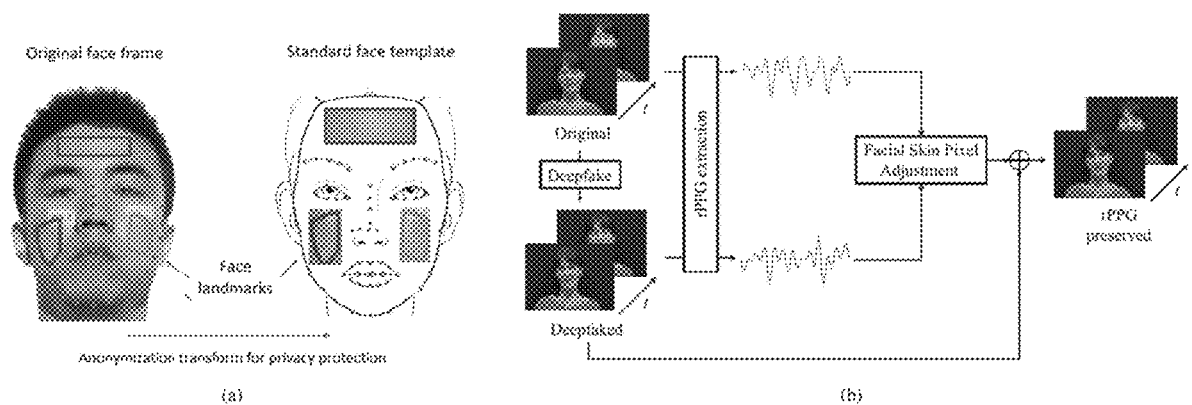
FIG. 12(a) illustrates an example of privacy protection method based on spatial warping, according to an embodiment.
FIG. 12(b) illustrates an example of privacy protection method based on a face swap procedure, according to one embodiment.

Some embodiments can leverage the preprocessing steps of facial landmark detection to identify relevant skin regions and assess the confidence of such segmentation. To remove the identifying visual data to an individual, an embodiment can determine and apply a geometric transformation of the high-confidence skin region to a canonical face template. Vector-field based warping such as those used in computer graphics to provide special visual effects of morphing can serve as one option. The mapping removes the specific facial structure unique to the individual, and synthesizes an avatar with a standard face template and active facial pixels being "transplanted" from the original face. Attention is paid to preserving subtle movements that may contain physiologic information such as those found in breathing. FIG. 12 illustrates an example of an anonymization transform process for privacy protection, according to an embodiment. In particular, FIG. 12(a) illustrates an example of privacy protection based on spatial warping, and FIG. 12(b) illustrates an example based on a face swap procedure.

In certain embodiments, additional approaches to privacy protective transform may include using deep neural network-based approach to "change" the identifying facial features to a different person, as if performing a "forgery", while preserving the skin region in terms of temporal variation. Along this line, it is noted that the techniques of so-called deepfakes enable the change or swap of a face in an original video, but these procedures that have been generally intended for forgery may weaken, change, or eliminate physiological signals on the face (e.g., rPPG). Therefore, in order to address the needs of privacy protection for data collection of face video based physiological monitoring, certain embodiments provide a protection framework to preserve the rPPG signal while removing privacy sensitive facial structures by adjusting the skin pixels in the facial region, which is illustrated in the example of FIG. 12(b). As discussed above, for rPPG analysis, the POS can be employed to map facial videos to pulse signals. This method first extracts the intensity variations in RGB channels via spatial averaging within the facial region in the video frames, and then the pulse signal is derived from the RGB signal, for example, by projecting the 3-channel signal onto the POS subspace.

Certain embodiments provide post-processing of facial skin pixel adjustment based on the extracted pulse signal. $C_o$ and Cf are denoted as the 3-channel signal after spatial averaging in the original video and the deepfaked video, respectively; δ denotes the perturbation imposed onto Cf to preserve the rPPG signals. Then, we have the rPPG preserved signal $\hat{C}f$=Cf+δ. Note that $C_o$, Cf, δ, and $\hat{C}f$ are vectors with length N, where N is the number of frames in the video. $C_o$ and $\hat{C}f$ are projected onto the POS subspace, respectively, and then the Pearson correlation coefficient is computed. The objective function is defined as:

$$\min_{\delta} -\rho(POS(C_o), POS(\hat{C}_f)) + \lambda \|\delta\|_2^2 \quad (17)$$

The first term governs the similarity of the rPPG signals in the original video and the deepfaked one and the second term confines the imposed perturbation small. Since the objective function is differentiable, an embodiment can leverage a gradient-based solver (e.g., Adam) to solve the optimization problem in (17).

After obtaining the perturbation vector δ, δ(n) can be added to every skin pixel on the facial region in the n-th frame of the deepfaked video to adjust the projection of $\hat{C}f$ closer to $C_o$ on the POS subspace. However, due to the quantization of pixel values in the video frames, the decimal part of δ has to be discarded when we adjust the pixels with the perturbation δ in the deepfaked video frames. For example, if the entry δ(n) is a pure decimal (i.e., |δ(n)|<1), the quantized perturbation on every skin pixel in the n-th frame is 0, which means no adjustment is executed on this frame. An embodiment uses randomized adjustment to render the decimal perturbation in an average sense. For n-th frame, the skin pixels may be adjusted in the amount of either ⌊δ(n)⌋ with probability p or ⌈δ(n)⌉ with probability 1−p, where the following equation should hold true:

$$\lfloor \delta(n) \rfloor \cdot p + \lceil \delta(n) \rceil \cdot (1 - p) = \delta(n). \quad (18)$$

By solving (18), p=⌈δ(n)⌉−δ(n) can be obtained. It is noted that the POS method is one example implementation in rPPG analysis, however some embodiments are not limited to POS and can also utilize other rPPG analysis modules as a substitution.

Furthermore, in certain embodiments, a set of metrics can be used to evaluate the effect of privacy-protective de-identification, and quantitatively assess the impact on physiological monitoring, such as HR detection accuracy, before and after such anonymization warping. Such a privacy protective transform can provide a promising vehicle to create an anonymized dataset that retains facial region's color variations and subtle movement, in addition to the conventional physiological reference data.

Figure 13:
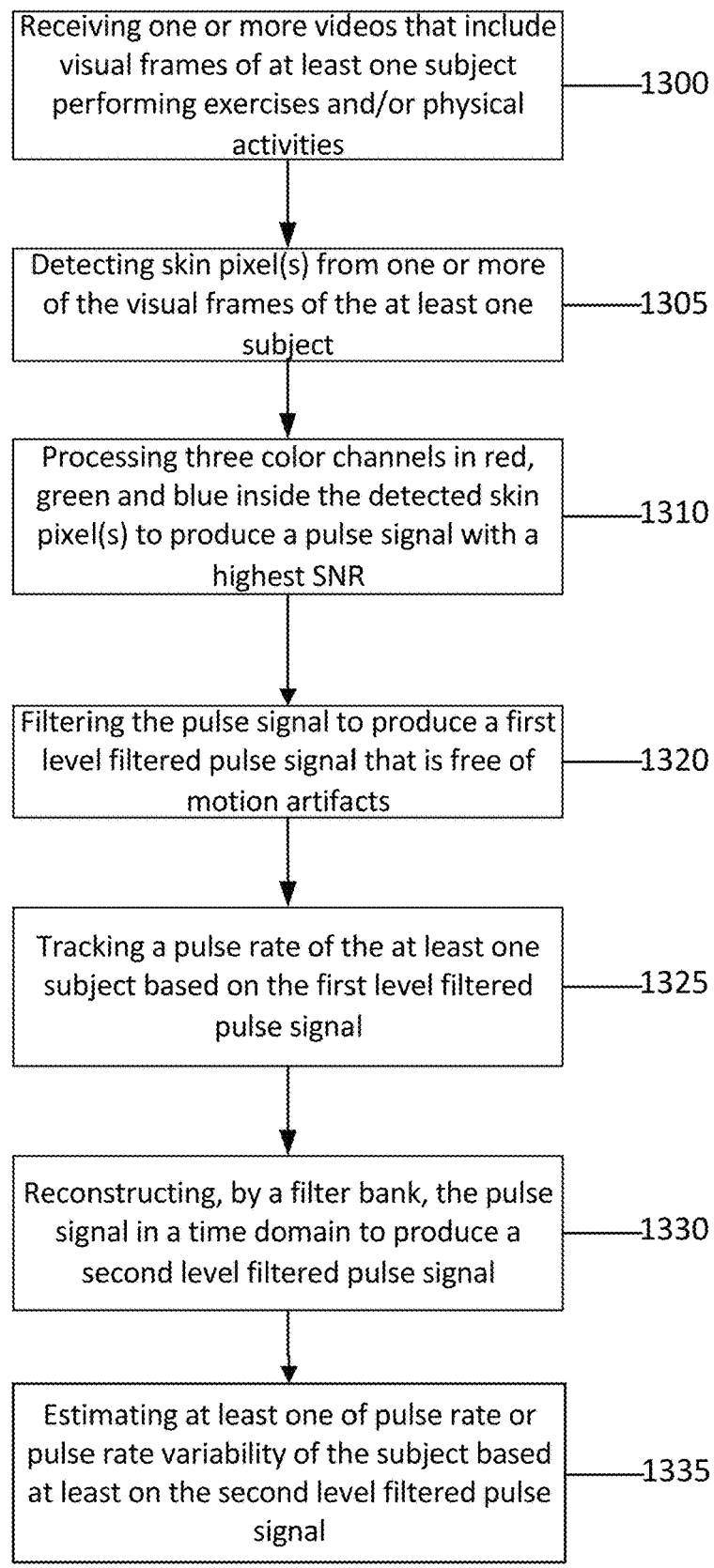
FIG. 13 illustrates an example remote photoplethysmography (rPPG) method, according to an embodiment.

FIG. 13 illustrates an example flow diagram of a remote photoplethysmography (rPPG) method, according to an example embodiment. For instance, the method of FIG. 13 may be configured to measure pulse rate and/or pulse rate variability of one or more subjects. In certain embodiments, the method of FIG. 14 may be performed by the system of FIG. 7 and/or apparatus of FIG. 6, discussed above. As illustrated in the example of FIG. 13, the method may include, at 1300, receiving one or more videos that include visual frames of at least one subject performing exercises and/or physical activities. For example, the videos may be captured by a camera included in the system.

As further illustrated in the example of FIG. 13, the method may include, at 1305, detecting at least one skin pixel from one or more of the visual frames of the at least one subject captured on the video. As discussed in detail above, the visual frames of the subject's face or skin can then be analyzed to measure variations in skin color, and heart rate or heart rate variation data, such as pulse rate variability, can then be estimated using the variation measurements. In an embodiment, the detecting 1305 may include rejecting a plurality of non-skin pixels and pixels that are dominated by specular reflection from the visual frames and retaining the skin pixels from the visual frames. In some embodiments, the detecting 1305 may include learning a probability distribution of the at least one subject's skin pixel based on colors of pixels collected from a region of interest (ROI) in one or more of the frames of the videos, as discussed in detail above. For instance, in one embodiment, the probability distribution may be learned based on the colors of pixels collected from a ROI in the first few frames of the videos, such as the first ten to twenty frames.

In the example of FIG. 13, the method may include, at 1310, processing three color channels in red, green and blue inside the detected at least one skin pixel to produce a pulse signal with a highest pulse signal-to-noise ratio (SNR). For instance, in an embodiment, the processing 1310 may include spatially averaging three color channels in red, green and blue inside the detected at least one skin pixel to produce a red, green, blue (RGB) face color signal, as discussed in detail above, and then pulse color mapping the face color signal to a color direction that produces a pulse signal with the highest pulse SNR. In an embodiment, the pulse color mapping may include using a recurrent neural network (RNN) with long short-term memory (LSTM) units to map a sequence of the visual frames to a label signal that is used for tracking of the pulse signal and respiration pattern, as discussed in detail above.

As also illustrated in the example of FIG. 13, the method may include, at 1320, filtering, for example by a NLMS filter, the pulse signal to remove or reduce motion artifacts, i.e., to produce a first level filtered pulse signal that is free of motion artifacts (or that has reduced or mitigated motion artifacts), as shown above. In one embodiment, the filtering 1320 may include estimating a motion of a face of the subject in horizontal and vertical directions, and using the estimated face motion to approximate and mitigate a motion residue term in the face color signal, as discussed above.

In the example of FIG. 13, the method may include, at 1325, using a frequency trace tracking method to track a pulse rate of the at least one subject based on the first level filtered pulse signal. The method may then include, at 1330, reconstructing the pulse signal in a time domain to produce a second level filtered pulse signal. In an embodiment, the reconstructing 1330 may be performed by a filter bank, as discussed above. In certain embodiments, the filter bank may be a filter bank with an adaptive subband modification layer configured for precise bandpass operation to reconstruct the pulse signal in the time domain. According to an embodiment, the filter bank may include a spectrum modification layer to suppress noise that is outside a frequency range of the pulse signal, as discussed in detail above. The method may then include, at 1335, estimating at least one of pulse rate or pulse rate variability of the at least one subject based at least on the second level filtered pulse signal, and optionally outputting the estimate of the pulse rate and/or pulse rate variability.

In some embodiments, the method may include removing identifying visual data of the at least one subject, for example, by applying a geometric transformation of relevant skin regions of the at least one subject to remove and replace facial structures that are unique to the at least one subject.

Therefore, certain example embodiments provide several technical improvements, enhancements, and/or advantages. Various example embodiments can, for example, provide a highly precise motion compensation scheme with the help of optical flow and use motion information as a cue to adaptively remove ambiguous frequency components for improving heart rate estimates. Experimental results demonstrate that example embodiments can achieve highly precise estimation with an average error of approximately 1.1 beats per minute (BPM) or just 0.58% in relative error. Additional embodiments provide improvements relating to video based physiological monitoring or rPPG including, but not limited to, providing improved reliability in skin detection, complementary means of handling motion and improving robustness, effective noise mitigation for extracting clean heartbeat PPG signal for deriving IBI that forms a basis for HRV/PRV analysis from video, and privacy protection techniques for protecting the privacy of sensitive data containing visual and physiological information of users.

In some example embodiments, the functionality of any of the methods, processes, signaling diagrams, algorithms or flow charts described herein may be implemented by software and/or computer program code or portions of code stored in memory or other computer readable or tangible media, and executed by a processor.

In some example embodiments, an apparatus may be included or be associated with at least one software application, module, unit or entity configured as arithmetic operation(s), or as a program or portions of it (including an added or updated software routine), executed by at least one operation processor. Programs, also called program products or computer programs, including software routines, applets and macros, may be stored in any apparatus-readable data storage medium and include program instructions to perform particular tasks.

A computer program product may comprise one or more computer-executable components which, when the program is run, are configured to carry out some example embodiments. The one or more computer-executable components may be at least one software code or portions of it. Modifications and configurations required for implementing functionality of an example embodiment may be performed as routine(s), which may be implemented as added or updated software routine(s). Software routine(s) may be downloaded into the apparatus.

As an example, software or a computer program code or portions of it may be in a source code form, object code form, or in some intermediate form, and it may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality may be performed by hardware or circuitry included in an apparatus, for example through the use of an application specific integrated circuit (ASIC), a programmable gate array (PGA), a field programmable gate array (FPGA), or any other combination of hardware and software. In yet another example embodiment, the functionality may be implemented as a signal, a non-tangible means that can be carried by an electromagnetic signal downloaded from the Internet or other network.

According to an example embodiment, an apparatus, such as a node, device, or a corresponding component, may be configured as circuitry, a computer or a microprocessor, such as single-chip computer element, or as a chipset, including at least a memory for providing storage capacity used for arithmetic operation and an operation processor for executing the arithmetic operation.

One skilled in the art will readily understand that the example embodiments as discussed above may be practiced with steps in a different order, and/or with hardware elements in configurations which are different than those which are disclosed. Therefore, although some embodiments have been described based upon these example preferred embodiments, it would be apparent to those of skill in the art that certain modifications, variations, and alternative constructions would be apparent, while remaining within the spirit and scope of example embodiments. In order to determine the metes and bounds of the example embodiments, therefore, reference should be made to the appended claims.

We claim:

1. A method of remote photoplethysmography (rPPG), comprising:
 receiving one or more videos that include visual frames of at least one subject performing physical activity;
 detecting at least one skin pixel from one or more of the visual frames of the at least one subject;
 processing three color channels in red, green and blue inside the detected at least one skin pixel to produce a pulse signal with a high pulse signal-to-noise ratio (SNR);
 filtering, by a normalized least mean square filter, the pulse signal to produce a first level filtered pulse signal that is free of motion artifacts;
 using a frequency trace tracking method to track a pulse rate of the at least one subject based on the first level filtered pulse signal;

reconstructing the pulse signal in a time domain to produce a second level filtered pulse signal; and
estimating at least one of pulse rate or pulse rate variability of the at least one subject based at least on the second level filtered pulse signal;
wherein the restructuring employs a filter bank comprises a spectrum modification layer to suppress noise that is outside a frequency range of the pulse signal.

2. The method of claim 1, wherein the detecting comprises rejecting a plurality of non-skin pixels and pixels that are dominated by specular reflection from the visual frames and retaining the skin pixels from the visual frames.

3. The method of claim 1, wherein the detecting comprises learning a probability distribution of the at least one subject's skin pixel based on colors of pixels collected from a region of interest in one or more of the frames of the videos.

4. The method of claim 1, wherein the filtering comprises estimating a motion of a face of the subject in horizontal and vertical directions, and using the estimated face motion to approximate and mitigate a motion residue term in the face color signal.

5. The method of claim 1, further comprising:
removing identifying visual data of the at least one subject by applying a geometric transformation of relevant skin regions of the at least one subject to remove and replace facial structures that are unique to the at least one subject.

6. A method of remote photoplethysmography (rPPG), comprising:
receiving one or more videos that include visual frames of at least one subject performing physical activity;
detecting at least one skin pixel from one or more of the visual frames of the at least one subject;
processing three color channels in red, green and blue inside the detected at least one skin pixel to produce a pulse signal with a high pulse signal-to-noise ratio (SNR);
filtering, by a normalized least mean square filter, the pulse signal to produce a first level filtered pulse signal that is free of motion artifacts;
using a frequency trace tracking method to track a pulse rate of the at least one subject based on the first level filtered pulse signal;
reconstructing the pulse signal in a time domain to produce a second level filtered pulse signal; and
estimating at least one of pulse rate or pulse rate variability of the at least one subject based at least on the second level filtered pulse signal;
wherein a mapping comprises using a recurrent neural network (RNN) with long short-term memory (LSTM) units to map a sequence of the visual frames to a label signal that is used for tracking of the pulse signal and a respiration pattern.

7. The method of claim 6, wherein the detecting comprises rejecting a plurality of non-skin pixels and pixels that are dominated by specular reflection from the visual frames and retaining the skin pixels from the visual frames.

8. The method of claim 6, wherein the detecting comprises learning a probability distribution of the at least one subject's skin pixel based on colors of pixels collected from a region of interest in one or more of the frames of the videos.

9. The method of claim 6, wherein the filtering comprises estimating a motion of a face of the subject in horizontal and vertical directions, and using the estimated face motion to approximate and mitigate a motion residue term in the face color signal.

10. The method of claim 6, wherein the reconstructing comprises reconstructing, by a filter bank, the pulse signal in the time domain.

11. The method of claim 10, wherein the filter bank comprises a spectrum modification layer to suppress noise that is outside a frequency range of the pulse signal.

12. The method of claim 6, further comprising:
removing identifying visual data of the at least one subject by applying a geometric transformation of relevant skin regions of the at least one subject to remove and replace facial structures that are unique to the at least one subject.

13. A remote photoplethysmography (rPPG) system, comprising:
at least one processor; and
at least one non-transitory computer-readable medium comprising computer program code, the at least one non-transitory computer-readable medium and the computer program code configured, with the at least one processor, to cause the system at least to perform:
receiving one or more videos that include visual frames of at least one subject performing physical activity;
detecting at least one skin pixel from one or more of the visual frames of the at least one subject;
processing three color channels in red, green and blue inside the detected at least one skin pixel to produce a pulse signal with a high pulse signal-to-noise ratio (SNR);
filtering, by a normalized least mean square filter, the pulse signal to produce a first level filtered pulse signal that is free of motion artifacts;
using a frequency trace tracking method to track a pulse rate of the at least one subject based on the first level filtered pulse signal;
reconstructing the pulse signal in a time domain to produce a second level filtered pulse signal; and
estimating at least one of pulse rate or pulse rate variability of the at least one subject based at least on the second level filtered pulse signal;
wherein the restructuring employs a filter bank comprises a spectrum modification layer to suppress noise that is outside a frequency range of the pulse signal.

14. The system of claim 13, wherein the detecting comprises rejecting a plurality of non-skin pixels and pixels that are dominated by specular reflection from the visual frames and retaining the skin pixels from the visual frames.

15. The system of claim 13, wherein the detecting comprises learning a probability distribution of the at least one subject's skin pixel based on colors of pixels collected from a region of interest in one or more of the frames of the videos.

16. The system of claim 13, wherein a mapping comprises using a recurrent neural network (RNN) with long short-term memory (LSTM) units to map a sequence of the visual frames to a label signal that is used for tracking of the pulse signal and a respiration pattern.

17. The system of claim 13, wherein the filtering comprises estimating a motion of a face of the subject in horizontal and vertical directions, and using the estimated face motion to approximate and mitigate a motion residue term in the face color signal.

18. The system of claim 13, wherein the at least one memory and computer program code are configured, with the at least one processor, to cause the system at least to perform:

removing identifying visual data of the at least one subject by applying a geometric transformation of relevant skin regions of the at least one subject to remove and replace facial structures that are unique to the at least one subject.

\* \* \* \* \*